United States Patent
Yamazaki et al.

(10) Patent No.: US 12,334,219 B2
(45) Date of Patent: Jun. 17, 2025

(54) DIAGNOSIS AND TREATMENT SUPPORT SYSTEM

(71) Applicant: CANON MEDICAL SYSTEMS CORPORATION, Otawara (JP)

(72) Inventors: Yudai Yamazaki, Nasushiobara (JP); Longxun Piao, Nasushiobara (JP); Kosuke Arita, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 719 days.

(21) Appl. No.: 17/484,002

(22) Filed: Sep. 24, 2021

(65) Prior Publication Data
US 2022/0108801 A1    Apr. 7, 2022

(30) Foreign Application Priority Data
Oct. 1, 2020   (JP) .................................. 2020-167217

(51) Int. Cl.
*G16H 50/20*       (2018.01)
*G06F 40/20*       (2020.01)
(Continued)

(52) U.S. Cl.
CPC .............. *G16H 50/20* (2018.01); *G06F 40/20* (2020.01); *G16H 10/60* (2018.01); *G16H 15/00* (2018.01); *G16H 50/70* (2018.01)

(58) Field of Classification Search
CPC ........ G16H 50/20; G16H 10/60; G16H 15/00; G16H 50/70; G06F 40/20
(Continued)

(56) References Cited

U.S. PATENT DOCUMENTS

| 2004/0122702 A1* | 6/2004 | Sabol | G06Q 10/10 |
| | | | 706/45 |
| 2008/0133275 A1* | 6/2008 | Haug | G16H 50/20 |
| | | | 705/3 |

(Continued)

FOREIGN PATENT DOCUMENTS

| JP | 2016-502650 A | 1/2016 |
| JP | 2016-181137 A | 10/2016 |

(Continued)

OTHER PUBLICATIONS

Missing values in condition monitoring datasets (Year: 2020).*

(Continued)

*Primary Examiner* — Gregory Lultschik
(74) *Attorney, Agent, or Firm* — Oblon, McClelland, Maier & Neustadt, L.L.P.

(57) ABSTRACT

A diagnosis and treatment support system according to an embodiment has a storage apparatus and processing circuitry. The storage apparatus stores a trained model that infers information related to a state of a patient from an examination value for a predetermined examination item. Based on correlations between examination values for plural examination items, the processing circuitry calculates a conversion function that enables statistical derivation of a possible examination value for another examination item from an examination value or values for one or plural examination items, and generates, based on an inference obtained by inputting an examination value for an examination item included in diagnosis and treatment information on a target patient and the examination value for the predetermined examination item derived by the conversion function from the examination value into the trained model, diagnosis and treatment support information for the target patient.

11 Claims, 13 Drawing Sheets

(51) Int. Cl.
  *G16H 10/60* (2018.01)
  *G16H 15/00* (2018.01)
  *G16H 50/70* (2018.01)

(58) Field of Classification Search
  USPC .......................................... 705/2, 3; 706/12
  See application file for complete search history.

(56) References Cited

U.S. PATENT DOCUMENTS

| | | | |
|---|---|---|---|
| 2012/0022844 A1* | 1/2012 | Teixeria ............... | A61B 5/0205 703/11 |
| 2015/0278470 A1 | 10/2015 | Bakker et al. | |
| 2020/0005900 A1* | 1/2020 | Cha ........................ | G16B 40/00 702/19 |

FOREIGN PATENT DOCUMENTS

| | | |
|---|---|---|
| JP | 2020-154723 A | 9/2020 |
| WO | WO 2019/022085 A1 | 1/2019 |

OTHER PUBLICATIONS

Neural Networks for Mulivariate Time Series with Missing Values (Year: 2018).*
Mathieu Lepot, Jean-Baptiste Aubin and Francois H.L.R. Clemens—Interpolation in Time Series: An Introductive Overview of Existing Methods, Their Performance Criteria and Uncertainty Assessment, MDPI, Oct. 17, 2017 (Year: 2017).*
Hang Liu, You yuan Wang and WeiGen Chen—Three-step imputation of missing values in condition monitoring datasets, IET Journals, Jul. 1, 2020 (Year: 2020).*
Zhengping Che, Sanjay Purushotham, Kyunghyun Cho, David Sontag, and Yan Liu, Recurrent Neural Networks for Multivariate Time Series with Missing Values, Scientific Reports, Apr. 17, 2018. (Year: 2018).*
Lipton et al, Modeling Missing Data in Clinical Time Series with RNNs, 2016, Proceedings of Machine Learning for Healthcare, JMLR W&C V.56 (Year: 2016).*
Japanese Office Action issued on Jul. 9, 2024 in Japanese Patent Application No. 2020-167217, 2 pages.
Japanese Office Action issued Oct. 8, 2024 in Japanese Patent Application No. 2020-167217, 2 pages.

* cited by examiner

| PATIENT ID | DATE | EXAMINATION INFORMATION | | | IMAGE INFORMATION | DESCRIPTION INFORMATION |
|---|---|---|---|---|---|---|
| | | BLOOD PRESSURE | NT-proBNP | MYOCARDIAL TROPONIN I | | |
| 0001 | 01.01 | 102 | 18 | 20 | ... | ... |
| 0001 | 01.02 | 92 | 20 | 22 | ... | ... |
| 0002 | 02.01 | 73 | 53 | 28 | ... | ... |
| 0002 | 02.03 | 80 | 42 | 14 | ... | ... |
| 0003 | 01.10 | 91 | 102 | 20 | ... | ... |
| 0003 | 01.11 | 89 | 101 | 11 | ... | ... |
| 0003 | 01.13 | 93 | 90 | 30 | ... | ... |
| ⋮ | ⋮ | ⋮ | ⋮ | ⋮ | ⋮ | ⋮ |

FIG.6
| PATIENT ID | DATE | IMAGE INFORMATION | EXAMINATION INFORMATION |
|---|---|---|---|
| | | | CTR |
| 0001 | 01.01 |  | 52 |
| 0002 | 02.03 |  | 42 |
FIG.7
| ID | OUTPUT | INPUT | CONVERSION FUNCTION | PRECISION | FREQUENCY |
|---|---|---|---|---|---|
| 1 | $x_1$ | $x_2, x_3$ | $P(x_1|x_2, x_3)=f(x_2, x_3)$ | 3.2 | 0.6 |
| 2 | $x_1$ | $x_2$ | $P(x_1|x_2)=f(x_2)$ | 10.2 | 1.2 |
| 3 | $x_1$ | $x_3$ | $P(x_1|x_3)=f(x_3)$ | 0.9 | 0.3 |
| 4 | $x_2$ | $x_1, x_3$ | $P(x_2|x_1, x_3)=f(x_1, x_3)$ | 3.2 | 0.6 |
| 5 | $x_2$ | $x_1$ | $P(x_2|x_1)=f(x_1)$ | 0.1 | 1.2 |
| 6 | $x_2$ | $x_3$ | $P(x_2|x_3)=f(x_3)$ | 2.1 | 0.3 |
| ⋮ | ⋮ | ⋮ | ⋮ | ⋮ | ⋮ |

FIG.8

| ID | OUTPUT | INPUT | SAMPLE DATA | CONVERSION FUNCTION | PRECISION | FREQUENCY |
|---|---|---|---|---|---|---|
| 1 | $x_1$ | $x_2, x_3$ | PATIENT ID:0001 | $P(x_1|x_2, x_3)=f(x_2, x_3)$ | 3.2 | 0.6 |
| 2 | $x_1$ | $x_2$ | PATIENT ID:0001 | $P(x_1|x_2)=f(x_2)$ | 10.2 | 1.2 |
| 3 | $x_1$ | $x_3$ | PATIENT ID:0001 | $P(x_1|x_3)=f(x_3)$ | 0.9 | 0.3 |
| 4 | $x_2$ | $x_1, x_3$ | HEART FAILURE PATIENT | $P(x_2|x_1, x_3)=f(x_1, x_3)$ | 3.2 | 0.6 |
| 5 | $x_2$ | $x_1$ | HEART FAILURE PATIENT | $P(x_2|x_1)=f(x_1)$ | 0.1 | 1.2 |
| 6 | $x_2$ | $x_3$ | HEART FAILURE PATIENT | $P(x_2|x_3)=f(x_3)$ | 2.1 | 0.3 |
| ⋮ | ⋮ | ⋮ | ⋮ | ⋮ | ⋮ | ⋮ |

FIG.9

| ID | OUTPUT | INPUT | CONVERSION FUNCTION | PRECISION | FREQUENCY | WEIGHTED PRECISION |
|---|---|---|---|---|---|---|
| 1 | $x_1$ | $x_2, x_3$ | $P(x_1|x_2, x_3)=f(x_2, x_3)$ | 3.2 | 0.6 | 5.33 |
| 2 | $x_1$ | $x_2$ | $P(x_1|x_2)=f(x_2)$ | 10.2 | 1.2 | 8.5 |
| 3 | $x_1$ | $x_3$ | $P(x_1|x_3)=f(x_3)$ | 0.9 | 0.3 | 3 |
| ⋮ | ⋮ | ⋮ | ⋮ | ⋮ | ⋮ | ⋮ |

FIG.11
| PATIENT ID | DATE | BLOOD PRESSURE | IMAGE INFORMATION | CTR (ESTIMATE) | CTR (SMALLEST) | CTR (LARGEST) |
|---|---|---|---|---|---|---|
| 1001 | 03.02 | 92 |  | 53 | 43 | 63 |
| 1002 | 04.03 | 80 |  | 34 | 30 | 36 |
| 1003 | 03.13 | 93 |  | 48 | 40 | 50 |
FIG.12
| PATIENT ID | DATE | DISEASE NAME | RISK (ESTIMATE) | RISK (MINIMUM) | CTR WHEN RISK IS MINIMUM | RISK (MAXIMUM) | CTR WHEN RISK IS MAXIMUM |
|---|---|---|---|---|---|---|---|
| 1001 | 03.02 | HEART FAILURE | 80% | 75% | 45 | 83% | 63 |
| 1002 | 04.03 | HEART FAILURE | 64% | 62% | 31 | 65% | 35 |
| 1003 | 03.13 | HEART FAILURE | 32% | 30% | 40 | 33% | 49 |

FIG.13
| PATIENT ID | DATE | BLOOD PRES- SURE | IMAGE INFORMA- TION | CTR (ESTIMATE) | RELIABILITY | DISEASE NAME | RISK (ESTIMATE) | RISK (MINIMUM) | CTR WHEN RISK IS MINIMUM | RISK (MAXIMUM) | CTR WHEN RISK IS MAXIMUM |
|---|---|---|---|---|---|---|---|---|---|---|---|
| 1001 | 03.02 | 92 | 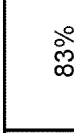 | 53 | 89% | HEART FAILURE | 80% | 75% | 45 | 83% | 63 |
| 1001 | 03.02 | 92 |  | 53 | 89% | LUNG CANCER | 72% | 70% | 45 | 83% | 63 |
| 1001 | 03.02 | 92 |  | 53 | 89% | DIABETES | 20% | 15% | 45 | 22% | 63 |
| 1002 | 04.03 | 80 | 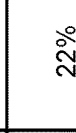 | 34 | 92% | HEART FAILURE | 64% | 62% | 31 | 65% | 35 |
| 1003 | 03.13 | 93 | 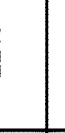 | 48 | 76% | HEART FAILURE | 32% | 30% | 40 | 33% | 49 |

DIAGNOSIS AND TREATMENT SUPPORT SYSTEM

CROSS-REFERENCE TO RELATED APPLICATIONS

This application is based upon and claims the benefit of priority from Japanese Patent Application No. 2020-167217, filed on Oct. 1, 2020; the entire contents of which are incorporated herein by reference.

FIELD

Embodiments described herein generally relate to diagnosis and treatment support systems.

BACKGROUND

Examinations and treatments in medical facilities have been conventionally conducted under the supervision of medical doctors (specialists) in diagnosis and treatment departments according to diseases of patients. Furthermore, in recent years, support technology including clinical decision support (CDS) systems has been proposed. Such a CDS system infers a state of a disease of a target patient to be diagnosed and treated and a risk of conversion using a model obtained by analysis of diagnosis and treatment information (such as examination results) of patients diagnosed and treated in the past by means of a technique, such as machine learning.

Although specialists in diagnosis and treatment departments are capable of adequately detecting diseases in their areas of expertise, they have difficulty in early detection of diseases outside their areas of expertise. Early detection of a disease outside a specialist's area of expertise may be attempted using the support technology mentioned above, but because different types of examinations are performed in different diagnosis and treatment departments, a support technique for another diagnosis and treatment department is unable to be used easily for the specialist's diagnosis and treatment department.

BRIEF DESCRIPTION OF THE DRAWINGS

FIG. 6 is a diagram illustrating an example of sample data obtained by the first obtaining function of the first embodiment;

FIG. 7 is a diagram illustrating an example of a data configuration of a conversion function table according to the first embodiment;

FIG. 8 is a diagram illustrating another example of the data configuration of the conversion function table according to the first embodiment;

FIG. 9 is a diagram for explanation of an example of operation of a converting function according to the first embodiment;

FIG. 11 is a diagram illustrating an example of a diagnosis and treatment information table according to the first embodiment;

FIG. 12 is a diagram illustrating an example of a support information table according to the first embodiment;

FIG. 13 is a diagram illustrating an example of a data configuration of display configuration information according to the first embodiment;

DETAILED DESCRIPTION

A diagnosis and treatment support system according to an embodiment has a storage apparatus and processing circuitry. The storage apparatus stores a trained model that infers information related to a state of a patient from an examination value for a predetermined examination item. The processing circuitry: calculates, on the basis of correlations between examination values for plural examination items included in diagnosis and treatment information on plural patients, a conversion function enabling statistical derivation of, from an examination value or values for one or plural examination items, a possible examination value for another examination item; generates, on the basis of an inference obtained by inputting an examination value for an examination item included in diagnosis and treatment information on a target patient into the trained model, support information for supporting diagnosis and treatment of the target patient; derives, on the basis of the conversion function, an examination value for a lacking examination item from an examination value for an examination item included in the diagnosis and treatment information on the target patient, in a case where examination items included in the diagnosis and treatment information on the target patient do not satisfy a requirement for the predetermined examination item; and causes the trained model to infer information related to a state of the target patient by inputting the derived examination value for the lacking examination item into the trained model.

Embodiments of a diagnosis and treatment support apparatus will hereinafter be described while reference is made to the drawings.

First Embodiment

Figure 1:
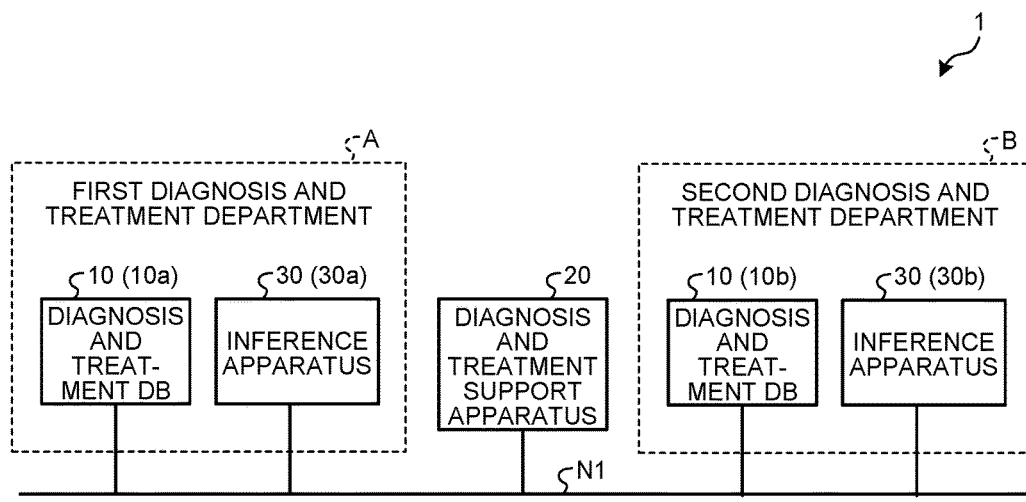
FIG. 1 is a diagram illustrating an example of a configuration of a diagnosis and treatment support system according to a first embodiment.

FIG. 1 is a diagram illustrating an example of a configuration of a diagnosis and treatment support system according to a first embodiment. As illustrated in FIG. 1, a diagnosis and treatment support system 1 has a diagnosis and treatment DB 10, a diagnosis and treatment support apparatus 20, and an inference apparatus 30. The diagnosis and treatment DB 10, the diagnosis and treatment support apparatus 20, and the inference apparatus 30 are installed in a medical facility, such as a hospital, for example, and connected to one another via a network N1, such as an in-hospital network, to enable communication among them.

The diagnosis and treatment DB 10 and the inference apparatus 30 are provided in each diagnosis and treatment department in the medical facility, for example. FIG. 1 illustrates an example in which the diagnosis and treatment DB 10 (10a or 10b) and the inference apparatus 30 (30a or 30b) are provided in each of a first diagnosis and treatment department A and a second diagnosis and treatment department B. For example, the first diagnosis and treatment department A is a department of respiratory medicine and the second diagnosis and treatment department B is a department of cardiovascular internal medicine.

The diagnosis and treatment DB 10 is configured to include a database storing therein diagnosis and treatment information on plural patients. The diagnosis and treatment DB 10 is an integrated management apparatus that obtains various types of diagnosis and treatment information from various medical information systems, such as an electronic medical record system, a picture archiving and communication system (PACS), a radiology department system, and a specimen examination system, and manages the diagnosis and treatment information obtained. FIG. 1 illustrates an example in which a dedicated diagnosis and treatment DB 10 is provided for each diagnosis and treatment department, but without being limited to this example, a diagnosis and treatment DB 10 formed of a signal or plural storage apparatuses may be shared by all of the diagnosis and treatment departments.

The diagnosis and treatment DB 10 stores therein diagnosis and treatment information related to patients, in association with patient IDs identifying the respective patients. The diagnosis and treatment information includes, for example, examination information, medical images, and document information. The examination information includes examination values obtained by various examinations. Specifically, the examination information is formed of an information group including dates on which the examinations were conducted, examination items indicating types of the examinations, and the examination values.

The examination information includes, in addition to examination items common to the respective diagnosis and treatment departments, examination items specific to that diagnosis and treatment department. The common examination items may be, for example, basic examination items indicating states of the bodies of the patients, such as blood pressures, heart rates, and body temperatures. The specific examination items differ from one diagnosis and treatment department to another, and may be, for a department of cardiovascular internal medicine, for example, examination items for NT-proBNP, myocardial troponin I, and cardiothoracic ratio (CTR).

The medical images are images of the patients obtained by various medical modalities, such as X-ray CT images obtained by an X-ray CT apparatus, MRI images obtained by an MRI apparatus, X-ray images obtained by an X-ray apparatus, and mammographic images obtained by a mammographic apparatus. The medical images are stored in association with, for example, additional information on types of the medical modalities and the imaged sites. Furthermore, the medical images are stored in association with information indicating dates on which the medical images were obtained.

The document information is document data, such as electronic medical records and report data, having information recorded therein, the information including examination values related to states of the bodies of the patients. The document information is stored in association with, for example, information indicating dates on which the document information was recorded. A state related to the body of a patient included in a medical image or document information will hereinafter be also referred to as an examination value.

The inference apparatus 30 is an apparatus related to clinical decision support (CDS) systems and computer-aided diagnosis (CAD) systems, for example. The inference apparatus 30 is implemented by a computer device, such as a personal computer (PC), a work station, or a server, for example. Furthermore, the inference apparatus 30 may be implemented by plural computer devices (a cloud) using cloud computing.

The inference apparatus 30 stores a trained model M1 (see FIG. 3) generated by a machine learning algorithm, such as logistic regression, a neural network, or deep learning. The trained model M1 has been trained beforehand to infer, from an examination value for a prescribed examination item, information related to a state of a patient, such as a disease name or a risk value for conversion quantitatively indicating the possibility of being diseased, when the examination value is input to the trained model M1. The trained model M1 generated may be specialized in an area treated by each diagnosis and treatment department by including an examination item specific to that diagnosis and treatment department in examination items in input data that are used (input) for training. In this embodiment, the trained model M1 specialized for the corresponding diagnosis and treatment department is assumed to be stored in the inference apparatus 30. Specifically, a trained model M1 specialized for the first diagnosis and treatment department A is stored in the inference apparatus 30a and a trained model M1 specialized for the second diagnosis and treatment department B is stored in the inference apparatus 30b.

When the inference apparatus 30 receives input data including an examination value for an examination item from a terminal apparatus in that diagnosis and treatment department or the diagnosis and treatment support apparatus 20, for example, the inference apparatus 30 inputs the received examination value for the examination item into the trained model M1. The inference apparatus 30 then outputs an inference, such as a disease name inferred by the trained model M1, to the apparatus that has input the input data. The inference apparatus 30 may be configured to notify an apparatus of the examination item in the input data, that is, the examination item used in the derivation of the inference, the apparatus being an apparatus that has accessed the inference apparatus 30.

By using diagnosis and treatment information on plural patients stored in the diagnosis and treatment DB 10, the diagnosis and treatment support apparatus 20 executes processing for calculating a conversion function described later. Furthermore, the diagnosis and treatment support apparatus 20 executes processing for supporting diagnosis and/or treatment (hereinafter, generally referred to as diagnosis and treatment) of a patient targeted (hereinafter, also referred to as a target patient) using the trained model M1 stored in the inference apparatus 30.

The diagnosis and treatment support apparatus 20 is implemented by a computer device, such as a PC, a work station, or a server, for example. In addition, the diagnosis and treatment support apparatus 20 may be implemented by plural computer devices (a cloud) using cloud computing.

Figure 2:
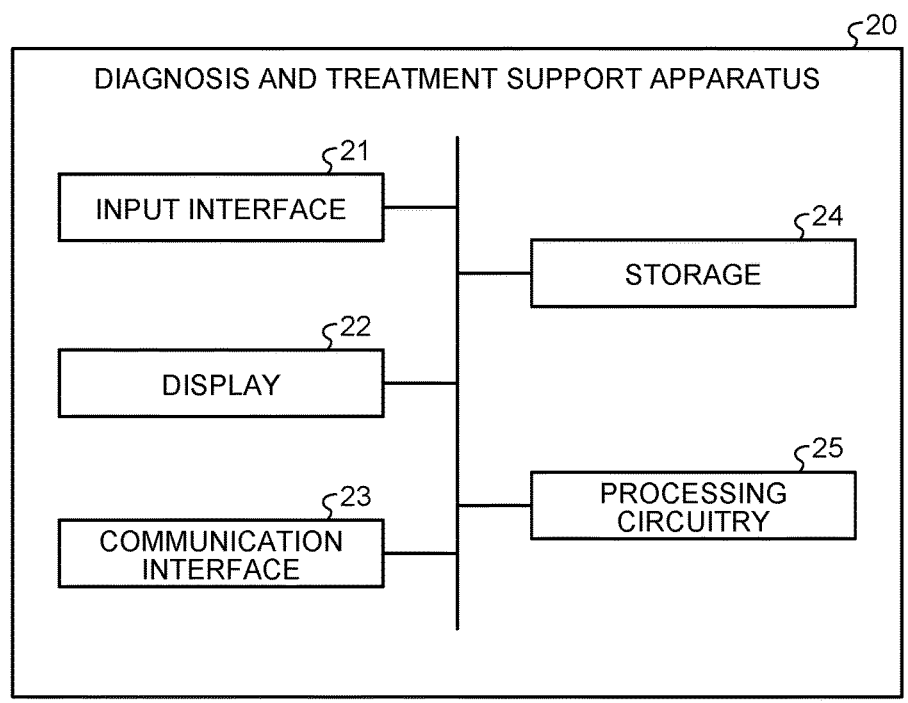
FIG. 2 is a diagram illustrating an example of a configuration of a diagnosis and treatment support apparatus according to the first embodiment.

A configuration of the diagnosis and treatment support apparatus 20 described above will be described next. FIG. 2 is a diagram illustrating an example of the configuration of the diagnosis and treatment support apparatus 20. As illustrated in FIG. 2, the diagnosis and treatment support apparatus 20 has an input interface 21, a display 22, a communication interface 23, a storage 24, and processing circuitry 25. The input interface 21, the display 22, the communication interface 23, the storage 24, and the processing circuitry 25 are connected to one another.

The input interface 21 receives various input operations from an operator, converts the input operations received into electric signals, and outputs the electric signals to the processing circuitry 25. For example, the input interface 21 is implemented by any of: a mouse and a keyboard; a trackball; switches; buttons; a joystick; a touchpad enabling an input operation by a touch on an operation surface; a touch screen having a display screen and a touchpad that have been integrated together; a non-contact input interface using an optical sensor; and a voice input interface.

Furthermore, the input interface 21 may be formed of a tablet terminal, for example, that is able to communicate with the diagnosis and treatment support apparatus 20. In addition, the input interface 21 does not necessarily include physical operating parts, such as a mouse and a keyboard. Examples of the input interface 21 include electric signal processing circuitry that receives an electric signal corresponding to an input operation from an external input device provided separately from the diagnosis and treatment support apparatus 20 and outputs this electric signal to the processing circuitry 25.

The display 22 displays various types of information. For example, under control of the processing circuitry 25, the display 22 displays a result of processing by the processing circuitry 25. Furthermore, the display 22 displays a graphical user interface (GUI) for receiving various instructions and various settings, for example, from an operator via the input interface 21. For example, the display 22 is a liquid crystal display or a cathode ray tube (CRT) display. The display 22 may be of the desktop type or may be formed of a tablet terminal that is able to communicate wirelessly with the diagnosis and treatment support apparatus 20, for example.

The communication interface 23 is an interface for communication with an external apparatus connected to the network N1. For example, the processing circuitry 25 is able to transfer various data to and from the diagnosis and treatment DB 10 and the inference apparatus 30, through the communication interface 23.

The storage 24 is implemented by, for example: a semiconductor memory element, such as a random access memory (RAM) or a flash memory; a hard disk; or an optical disk. For example, the storage 24 stores a program for a circuit to implement a function of the circuit, the circuit being included in the diagnosis and treatment support apparatus 20. Furthermore, the storage 24 stores various data and information, such as a conversion function table T1 (see FIG. 3) for holding conversion functions described later.

The processing circuitry 25 controls the overall processing of the diagnosis and treatment support apparatus 20. Furthermore, the processing circuitry 25 according to this embodiment has, as illustrated in FIG. 3, a first obtaining function 251, a calculating function 252, a second obtaining function 253, a converting function 254, a generating function 255, a display configuring function 256, and a displaying function 257.

Figure 3:
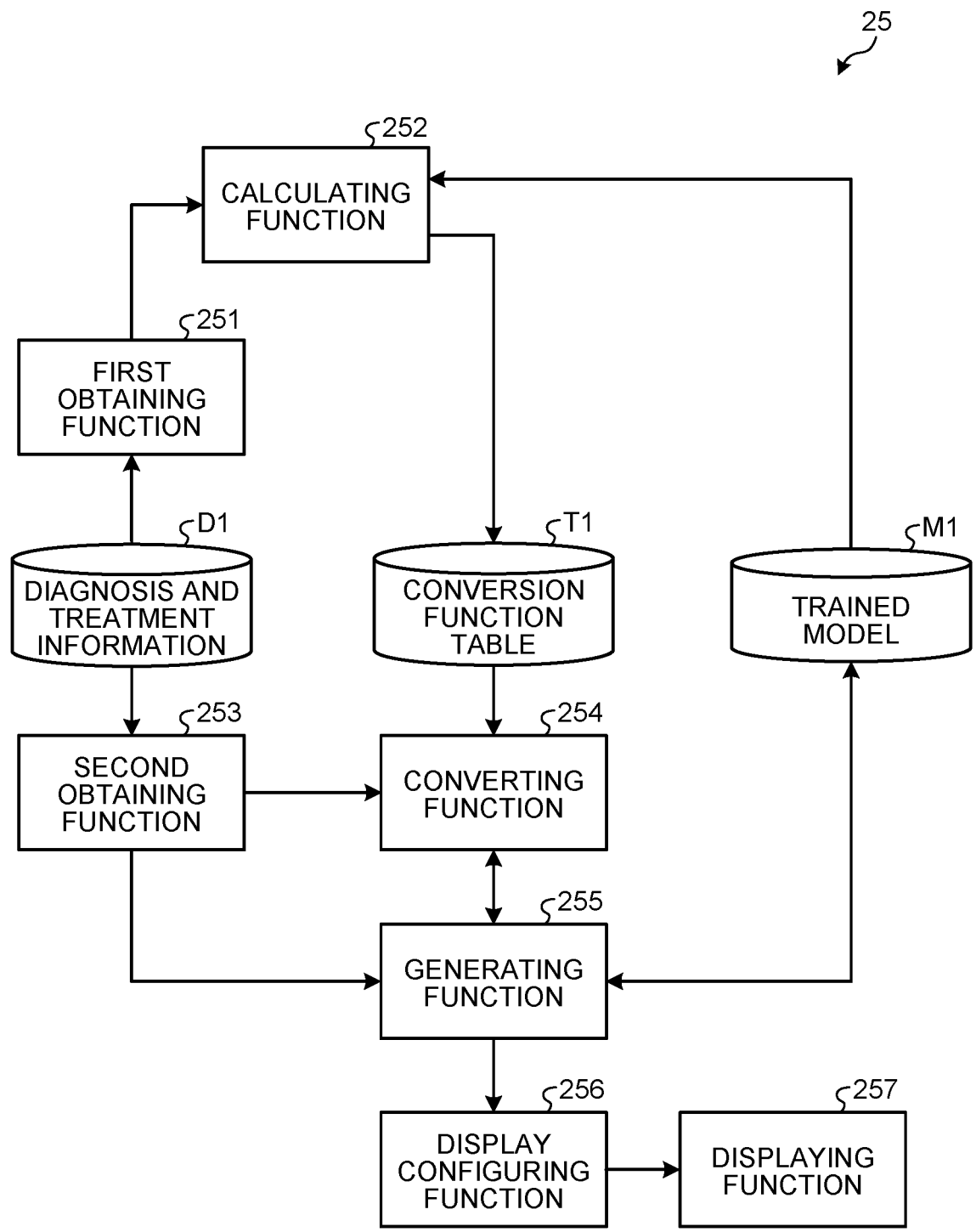
FIG. 3 is a diagram illustrating an example of components included in processing circuitry of the diagnosis and treatment support apparatus according to the first embodiment.

FIG. 3 is a diagram illustrating an example of components included in the processing circuitry 25 of the diagnosis and treatment support apparatus 20. For example, processing functions respectively executed by the first obtaining function 251, the calculating function 252, the second obtaining function 253, the converting function 254, the generating function 255, the display configuring function 256, and the displaying function 257 that are the components of the processing circuitry 25 illustrated in FIG. 3 have been stored in the storage 24 in the form of programs executable by a computer. The processing circuitry 25 is a processor that implements the functions corresponding to these programs by reading and executing the programs from the storage 24. In other words, the processing circuitry 25 that has read the programs has the functions illustrated in FIG. 3.

In FIG. 3, the first obtaining function 251, the calculating function 252, the second obtaining function 253, the converting function 254, the generating function 255, the display configuring function 256, and the displaying function 257 are implemented by the single piece of processing circuitry 25, but the processing circuitry 25 may be formed of a combination of plural independent processors and these processors may implement the functions by executing the programs. Furthermore, any of the processing functions that the processing circuitry 25 has may be implemented by being distributed to plural pieces of processing circuitry or integrated into a single processing circuitry, as appropriate.

In addition, the processing circuitry 25 may implement the functions by using a processor of an external apparatus connected via the network N1. For example, the processing circuitry 25 may implement the functions illustrated in FIG. 3 by reading and executing the programs corresponding to the functions from the storage 24 and using, as a computational resource, a server group (for example, a cloud) connected to the diagnosis and treatment support apparatus 20 via the network N1.

FIG. 3 illustrates diagnosis and treatment information D1, the conversion function table T1, and the trained model M1 as elements other than the functions of the processing circuitry 25. The diagnosis and treatment information D1 is diagnosis and treatment information stored in the diagnosis and treatment DB 10 (diagnosis and treatment DB 10a or diagnosis and treatment DB 10b). Furthermore, the conversion function table T1 is a storage unit for storing the later described conversion functions held in the storage 24, for example. In addition, the trained model M1 is a trained model stored in the inference apparatus 30 (inference apparatus 30a or inference apparatus 30b).

The first obtaining function 251 obtains, as sample data for calculation of a conversion function, the diagnosis and treatment information D1 on plural patients, the diagnosis and treatment information D1 having been stored in the diagnosis and treatment DB 10. The first obtaining function 251 may obtain diagnosis and treatment information D1 stored in both the diagnosis and treatment DB 10a and the diagnosis and treatment DB 10b, or may obtain diagnosis and treatment information D1 stored in one of the diagnosis and treatment DB 10a and the diagnosis and treatment DB 10b.

Furthermore, the first obtaining function 251 may obtain diagnosis and treatment information D1 corresponding to a predetermined condition. For example, the first obtaining function 251 may obtain diagnosis and treatment information D1 related to a particular patient ID. The first obtaining function 251 may also obtain, for example, diagnosis and treatment information D1 on patients with the same disease name or similar disease names.

A condition for obtaining the diagnosis and treatment information D1 may be freely set. Furthermore, the first obtaining function 251 may be configured to change the condition for the diagnosis and treatment information D1 to be obtained, by cooperating with the calculating function 252.

The calculating function 252 is an example of a calculating unit. On the basis of diagnosis and treatment information D1 (sample data) on plural patients obtained by the first obtaining function 251, the calculating function 252 calculates a conversion function enabling statistical derivation of, from an examination value or values for one or plural examination items included in the diagnosis and treatment information D1, a possible examination value for another examination item. The conversion function is, for example, a trained model trained by machine learning, or a model formula of simple regression analysis or multiple regression analysis.

Specifically, by analyzing relations between examination values for examination items included in the diagnosis and treatment information D1 using a technique, such as machine learning, the calculating function 252 calculates a conversion function enabling derivation of a probability distribution of possible examination values for any examination item, from an examination value for another examination item. Methods of calculating the conversion function are not particularly limited, but the conversion function is preferably calculated by a method (algorithm) according to the types of the examination items or characteristics of the examination values. For example, the calculating function 252 may calculate the conversion function using any of calculation methods (first to third calculation methods) described below.

First Calculation Method

In the first calculation method, the calculating function 252 collects, for each patient, diagnosis and treatment information D1 (examination information) of the same day assigned with the same date and treats the collected diagnosis and treatment information D1 as a data set for calculating a conversion function.

Figures 4, 5:
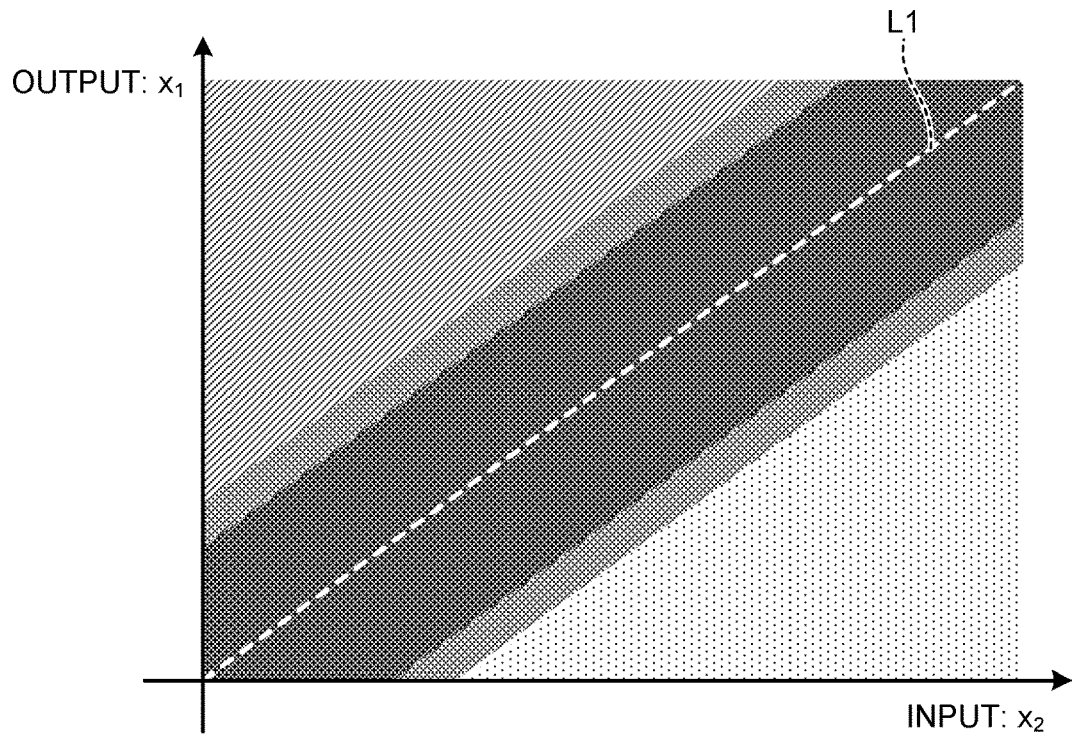
FIG. 4 is a diagram illustrating an example of sample data obtained by a first obtaining function of the first embodiment.
FIG. 5 is a diagram schematically illustrating a state of a probability distribution derived from a conversion function according to the first embodiment.

For example, it is assumed herein that the sample data obtained by the first obtaining function 251 have the content illustrated in FIG. 4. FIG. 4 is a diagram illustrating an example of the sample data obtained by the first obtaining function 251. In this case, the calculating function 252 treats, as a data set, examination information obtained on each of dates, "01.01", "01.02", "01.10", "01.11", "01.13", "02.01", and "02.03". The calculating function 252 performs setting to make data independent for each patient ID such that pieces of examination information of the same day for plural patients are not mixed.

Subsequently, the calculating function 252 learns relations between examination values for examination items included in each data set of examination information, by using a machine learning technique, such as a linear regression model or a neural network. On the basis of correlations between examination values for examination items included in the examination information, the calculating function 252 calculates, from an examination value for an examination item serving as a source of conversion, a conversion function enabling stochastic derivation of an examination value for another examination item resulting from the conversion.

For example, as expressed by Equation (1) below, in a case where an examination value for an examination item $x_2$ is input, when a probability distribution for output of an examination value for another examination item $x_1$ is $P(x_1|x_2)$, the calculating function 252 calculates a conversion function $f(x_2)$ enabling derivation of this $P(x_1|x_2)$.

$$P(x_1|x_2) = f(x_2) \quad (1)$$

For example, of three examination items, "Blood pressure", "NT-proBNP", and "Myocardial troponin I", that are included in examination information, "Myocardial troponin I" is assumed to be $x_1$ and "NT-proBNP" is assumed to be $x_2$. In this case, the calculating function 252 calculates a conversion function f(NT-proBNP) enabling derivation of a probability distribution P(myocardial troponin I|NT-proBNP) of possible examination values for myocardial troponin I correspondingly to an examination value for NT-proBNP.

FIG. 5 is a diagram schematically illustrating a state of a probability distribution $P(x_1|x_2)$ derived from a conversion function $(x_2)$. In FIG. 5, the horizontal axis corresponds to an examination value for an examination item $x_2$ to be input and the vertical axis corresponds to an examination value for an examination item $x_1$ to be output.

Furthermore, the shading illustrated in the background of the $x_1$-$x_2$ space represents a probability distribution of examination values for the examination item $x_1$, and the area higher in density is higher in probability of occurrence. A broken line L1 illustrated in the $x_1$-$x_2$ space corresponds to a regression formula approximating a distribution of values for the examination item $x_2$ where the probability is highest at respective values for the examination item $x_1$.

As illustrated in FIG. 5, using the conversion function $f(x_2)$ enables determination of, from an examination value for the examination item $x_2$, a probability distribution $P(x_1|x_2)$ of possible examination values for the examination item $x_1$. That is, the conversion function $f(x_2)$ enables output of a possible examination value for the examination item $x_1$ and its probability (hereinafter, also referred to as the reliability) from the input examination value for the examination item $x_2$.

Furthermore, the calculating function 252 comprehensively combines plural examination items forming examination information to calculate a conversion function for each combination of the examination items.

For example, in the example of FIG. 4, the calculating function 252 calculates a conversion function that enables derivation of, from an examination value or values for any one or two examination items of the three examination items forming the examination information, "Blood pressure", "NT-proBNP", and "Myocardial troponin I", of a probability distribution of examination values for another examination item. In this case, the calculating function 252 calculates nine conversion functions. A conversion function for deriving, from examination values for the two examination items $x_2$ and $x_3$, a probability distribution of examination values for the remaining one examination item $x_1$ may be expressed by Equation (2) below, for example, similarly to Equation (1) above.

$$P(x_1|x_2, x_3) = f(x_2, x_3) \quad (2)$$

On the basis of the type of input data input to a trained model M1, the calculating function 252 may determine a combination of examination items related to calculation of a conversion function. For example, in a case where input data for a trained model M1 are the examination items, "Blood pressure" and "NT-proBNP", the calculating function 252 may calculate a conversion function enabling derivation of a probability distribution for these examination items, "Blood pressure" and "NT-proBNP".

The calculating function 252 then stores the conversion function calculated, into a conversion function table T1. Furthermore, the calculating function 252 stores the precision obtained for the calculation of the conversion function and a condition for the examination information used in calculating the conversion function, for example, in association with the conversion function.

This precision is a probable error between the actual examination value for the examination item $x_1$ and the examination value for the examination item $x_1$ derived (estimated) from the conversion function. The precision may be calculated on the basis of, for example, a probability model, such as a normal distribution.

Furthermore, examples of the condition for the examination information include data characteristics of the examination information used in the calculation of the conversion function, the number of pieces of examination information included in the data set (the number of records), the number of days of the date counted as the diagnosis and treatment information D1 of the same one day, the number of examination items, and the number of patients, for example. The data characteristics of the examination information may be a patient ID or disease name in the examination information used in the calculation of the conversion function, for example. The disease name may be identified from description information associated with the patient ID, for example, or identified from other information (for example, recorded information on a result of diagnosis by a medical doctor) associated with the patient ID.

In this embodiment, the above described condition for the examination information is assumed to be expressed using an index value, "Frequency", calculated by Equation (3) below.

$$\text{Frequency=total number of records} \div (\text{number of days} \times \text{number of examination items} \times \text{number of patients}) \quad (3)$$

Second Calculation Method

In the second calculation method, the calculating function 252 collects, for each patient, chronologically consecutive pieces of diagnosis and treatment information D1, and treats the chronological data of the diagnosis and treatment information D1 collected as a data set for calculating a conversion function.

If sample data obtained by the first obtaining function 251 have the content in FIG. 4, for example, the calculating function 252 treats an examination information group of a patient ID, "0001", obtained on dates, "01.01" and "01.02", as a single set of chronological data. Furthermore, similarly, the calculating function 252 treats an examination information group of a patient ID, "0002", obtained on dates "02.01" and "02.03", as a single set of chronological data. There is examination information corresponding to three days for a patient ID, "0003", but to make conditions the same as those for the patient IDs, "0001" and "0002", each of an examination information group for "01.10" and "01.11", an examination information group for "01.11" and "01.13", and an examination information group for "01.10" and "01.13" is preferably treated as a single set of chronological data.

Subsequently, the calculating function 252 learns relations between examination values for examination items included in the examination information using a machine learning technique, such as a recurrent neural network (RNN) that is capable of handling chronological data. On the basis of correlations between the examination values for the examination items included in the examination information, the calculating function 252 calculates, from an examination value for an examination item serving as a source of conversion, a conversion function that enables stochastic derivation of an examination value for another examination item resulting from the conversion.

In this case, for example, the conversion function may be expressed by Equation (4) below.

$$P(x_1^t | x_2^t, x_1^{t-1}, x_2^{t-1}) = f(x_2^t, x_1^{t-1}, x_2^{t-1}) \quad (4)$$

The conversion function $f(x_2^t, x_1^{t-1}, x_2^{t-1})$ is for deriving a probability distribution $P(x_1^t | x_2^t, x_1^{t-1}, x_2^{t-1})$ of values, from an examination value $x_2^t$ at the time of a date and time t for an examination item $x_2$, an examination value $x_2^{t-1}$ at the time of a date and time t−1 therefor, and an examination value $x_1^{t-1}$ at the time of a date and time t−1 for another examination item $x_1$, the values being possible examination values $x_1^t$ at the time of a date and time t for that other examination item $x_1$.

Furthermore, similarly to the first calculation method, the calculating function 252 comprehensively combines plural examination items forming the examination information to calculate a conversion function for each combination of the examination items.

On the basis of the type of input data input to the trained model M1, the calculating function 252 may determine a combination of examination items related to calculation of a conversion function. Furthermore, in the above example, examination information corresponding to two days was treated as a single set of chronological data, but without being limited to this example, examination information corresponding to three days or more may be treated as a single set of chronological data to calculate a conversion function.

The calculating function 252 then stores the conversion function calculated, into the conversion function table T1. Furthermore, similarly to the first calculation method, the calculating function 252 stores the precision obtained for the calculation of the conversion function and a condition for the examination information used in calculating the conversion function, for example, in association with the conversion function. In this embodiment, the above described condition for the examination information is expressed using an index value, "Frequency", calculated by Equation (3) above.

Third Calculation Method

The calculating function 252 also calculates a conversion function that enables derivation of a probability distribution of examination values for a predetermined examination item from image information that is unstructured data. "Unstructured data" herein means data from which examination values are unable to be handled directly. For example, examination values for examination items forming examination information are able to be directly read and may thus be defined as "structured data". In contrast, image information or description information is "unstructured data" because processing for extracting examination values therefrom is needed. A method of calculating a conversion function from unstructured data will hereinafter be described as the third calculation method.

In the third calculation method, the calculating function 252 treats, as a data set for calculating a conversion function, each pair of image information and examination information of the same one day assigned with the same date.

For example, it is assumed now that sample data obtained by the first obtaining function 251 have the content illustrated in FIG. 6. FIG. 6 is a diagram illustrating an example of the sample data obtained by the first obtaining function 251.

In this case, the calculating function 252 treats, as a data set for calculating a conversion function, each of pairs of pieces of image information and examination values for CTR, the pairs having been obtained on dates, "01.01" and "02.03". The calculating function 252 performs setting to make data independent for each patient ID such that pieces of examination information on the same day for plural patients are not mixed.

Subsequently, the calculating function 252 performs learning using a machine learning technique, such as deep learning, that is able to handle relations between the image information and examination values for CTR both serving as a processed unit. On the basis of correlations between the image information and the examination values for CTR, the calculating function 252 calculates a conversion function that enables stochastic derivation of an examination value for CTR resulting from conversion, from image information serving as a source of the conversion. Using the conversion function enables derivation of a probability distribution of possible examination values for CTR, from image information.

In the example described above, the examination item derived from the image information is CTR, but the examination item derived from image information is not necessarily CTR and may be any examination item included in the examination information. However, an examination item to be derived is preferably an examination item related to the type of a medical modality or related to an imaged region captured in a medical image, such that the examination item derived does not become an examination item unrelated to the medical image.

A conversion function calculated by the third calculation method may be expressed by Equation (5) below, for example.

$$P(x_1|x_{img}) = f(x_{img}) \quad (5)$$

A conversion function $f(x_{img})$ is for deriving, from an examination value from image information $x_{img}$, a probability distribution $P(x_1|x_{img})$ of possible examination values for an examination item $x_1$, such as CTR, included in examination information.

The examination value from the image information $x_{img}$ may be the image information itself or a result of processing resulting from preprocessing of the image information. In the latter case, for example, the examination value from the image information $x_{img}$ may be a feature value extracted from the image information by a publicly known technique.

The calculating function 252 then stores the conversion function generated, into the conversion function table T1. Furthermore, the calculating function 252 stores the precision obtained for the calculation of the conversion function and a condition for the image information used in calculating the conversion function, for example, in association with the conversion function.

In addition, the calculating function 252 may calculate a conversion function for a pair of description information and examination information of the same one day assigned with the same date, by a technique similar to that described above. However, in this case, learning is performed using natural language processing or a machine learning technique that is able to handle correlations (or co-occurrence relations) between: wording of examination items or examination values indicating states of bodies of patients, the wording being included in the description information; and the examination values in the examination information. In this case, wording or terms to be extracted from the description information may be set beforehand.

The three calculation methods described above may be used by being combined with each other. For example, a conversion function may be calculated by combining the first calculation method with the third calculation method, the conversion function enabling derivation of a probability distribution of possible examination values for an examination item $x_1$ from an examination value for an examination item $x_2$ and image information $x_{img}$. Furthermore, for example, the first calculation method and second calculation method described above may be combined to be used by extracting wording, such as an examination value, from description information and treating information extracted as examination values for examination items $x_2$ and $x_3$.

FIG. 7 is a diagram illustrating an example of a data configuration of the conversion function table T1. As illustrated in FIG. 7, the conversion function table T1 has data items, such as "ID", "Output", "Input", "Conversion function", "Precision", and "Frequency".

Identification numbers for identifying conversion functions registered in the conversion function table T1 are stored in the "ID" column. Examination items resulting from conversion that are output by the conversion functions are stored in the "Output" column. Examination items input to the conversion functions and types of unstructured data (image information or description information) are stored in the "Input" column, for example. The conversion functions calculated by the calculating function 252 and addresses of storage destinations at which the conversion functions are stored are stored in the "Conversion function" column. Values of precision obtained at the time of calculation of the conversion functions are stored in the "Precision" column. Values of frequency calculated by Equation (3) above are stored in the "Frequency" column.

FIG. 8 is a diagram illustrating another example of the data configuration of the conversion function table T1. The conversion function table T1 in FIG. 8 has a data item, "Sample data", added to the data configuration of the conversion function table T1 described by reference to FIG. 7. Conditions related to the diagnosis and treatment information D1 (sample data) used at the time of calculation of the conversion functions are stored in this "Sample data" column. For example, in a case where a conversion function is calculated with sample data being limited to the diagnosis and treatment information D1 related to a particular patient or a particular disease name, information indicating that limitation condition is stored in the "Sample data" column.

As described above, the first obtaining function 251 and the calculating function 252 in the diagnosis and treatment support apparatus 20 calculate, from correlations between various examination values included in diagnosis and treatment information D1 on plural patients, a conversion function that enables derivation of, from an examination value of any type, a probability distribution of possible examination values of another type. In a case where an examination value or values for some of examination items are lacking, for example, using this conversion function enables derivation of a possible examination value for any lacking examination item, from the examination values for the other examination items.

In a case where the diagnosis and treatment information D1 has been obtained from the diagnosis and treatment DB 10a provided in the first diagnosis and treatment department A, applying (inputting) this diagnosis and treatment information D1 to the trained model M1 stored in the inference apparatus 30a of the same diagnosis and treatment department enables obtainment of an inference, such as a disease name adapted for the area of diagnosis and treatment of that same diagnosis and treatment department.

Furthermore, applying the diagnosis and treatment information D1 of the diagnosis and treatment DB 10a to the trained model M1 stored in the inference apparatus 30b of the second diagnosis and treatment department B enables obtainment of a disease name and any risk adapted for the area of diagnosis and treatment of the second diagnosis and treatment department B, and the state of the patient is thus able to be diagnosed and treated from various perspectives.

However, in a case where the diagnosis and treatment information D1 obtained from the diagnosis and treatment DB 10b is applied to the trained model M1 stored in the inference apparatus 30b of the second diagnosis and treatment department B, no inference may be able to be derived because items of input data used in inference of a disease name are different.

Therefore, in a case where some of items of input data needed for inference by a trained model M1 is/are lacking, by using the conversion function described above, the diagnosis and treatment support apparatus 20 executes processing for supplementing examination values with an examination value for any lacking examination item using an examination value for an existing examination item included in the diagnosis and treatment information D1. In the diagnosis and treatment support apparatus 20, on the basis of an inference obtained by input of the existing examination value included in the diagnosis and treatment information D1 and an examination value resulting from conversion derived using the conversion function into the trained model M1, processing is executed, the processing being for generating support information for supporting diagnosis and treatment of a target patient and providing the support information. Functions of the diagnosis and treatment support apparatus 20 related to this processing will be described below.

The second obtaining function 253 obtains diagnosis and treatment information D1 on a target patient, from a diagnosis and treatment DB 10. For example, the second obtaining function 253 obtains diagnosis and treatment information D1 on a target patient from the diagnosis and treatment DB 10a of the first diagnosis and treatment department A.

The target patient is specified by input of a patient ID of the patient targeted, via the input interface 21 or the communication interface 23, for example. Plural pieces of diagnosis and treatment information D1 (for plural days) on the target patient may be obtained instead of a single piece of diagnosis and treatment information D1 on the target patient. Furthermore, instead of just a single target patient, plural target patients may be specified. The diagnosis and treatment information D1 on the target patient obtained by the second obtaining function 253 is output to the converting function 254 and the generating function 255.

The converting function 254 is an example of a deriving unit. By cooperating with the generating function 255, the converting function 254 executes a conversion process for deriving, from an examination value for an existing examination item included in the diagnosis and treatment information D1 on the target patient, an examination value for another examination item (conversion).

Specifically, when the generating function 255 described later notifies the converting function 254 of a lacking examination item, on the basis of a conversion function stored in a conversion function table T1, the converting function 254 derives an examination value for the lacking examination item, from an examination value for an existing examination item included in the diagnosis and treatment information D1.

An example of operation of the converting function 254 will be described below. FIG. 9 is a diagram for explanation of the example of the operation of the converting function 254. FIG. 9 illustrates some of conversion functions stored in a conversion function table T1.

For example, in a case where a lacking examination item is $x_1$, the converting function 254 retrieves, from the conversion function table T1, a conversion function having the examination item $x_1$ registered in the "Output" column and having an existing examination item registered in the "Input" column, the existing examination item being included in the diagnosis and treatment information D1. For example, in a case where $x_2$ and $x_3$ are included as existing examination items in the diagnosis and treatment information D1, the converting function 254 specifies conversion functions having IDs, "1" to "3", in the conversion function table T1 of FIG. 9.

In a case where plural conversion functions corresponding to the search condition are available like in the above example, the converting function 254 selects one of the conversion functions on the basis of the precision and frequency stored in association with those conversion functions. For example, the converting function 254 may select a conversion function having the highest value of precision or may select a conversion function having the highest value of frequency.

Furthermore, by using Equation (6) below, for example, the converting function 254 may perform calculation to obtain weighted precision from the precision and frequency and select one of the conversion functions on the basis of a result of this calculation.

$$\text{Weighted precision} = \text{precision} \times \text{inverse of frequency} \qquad (6)$$

The smaller the value of the weighted precision calculated by Equation (6) above is, the higher the precision is. FIG. 9 illustrates the values of the weighted precision calculated by Equation (6) above. In this case, by selecting the conversion function having the smallest value of weighted precision, that is, the conversion function having the ID, "3", the converting function 254 is able to derive an examination value for a lacking examination item using the conversion function that is more precise.

The weighted precision may be calculated on the basis of Equation (7) below. In this case, the larger that value of the weighted precision calculated is, the higher the precision is, and the converting function 254 thus preferably selects the conversion function with the largest value of weighted precision.

$$\text{Weighted precision} = \text{precision} \times \text{frequency} \qquad (7)$$

Subsequently, by using the conversion function selected, the converting function 254 derives an examination value for a lacking examination item. Specifically, the converting function 254 reads the examination value for the examination item prescribed in the "Input" column for the conversion function selected, from the existing examination items included in the diagnosis and treatment information D1 on the target patient, and inputs the read examination value into the conversion function.

When the examination value for the examination item serving as a source of conversion is input to the conversion function, the conversion function enables output (derivation) of a possible examination value for the examination item resulting from the conversion, as a random variable.

Figure 10:
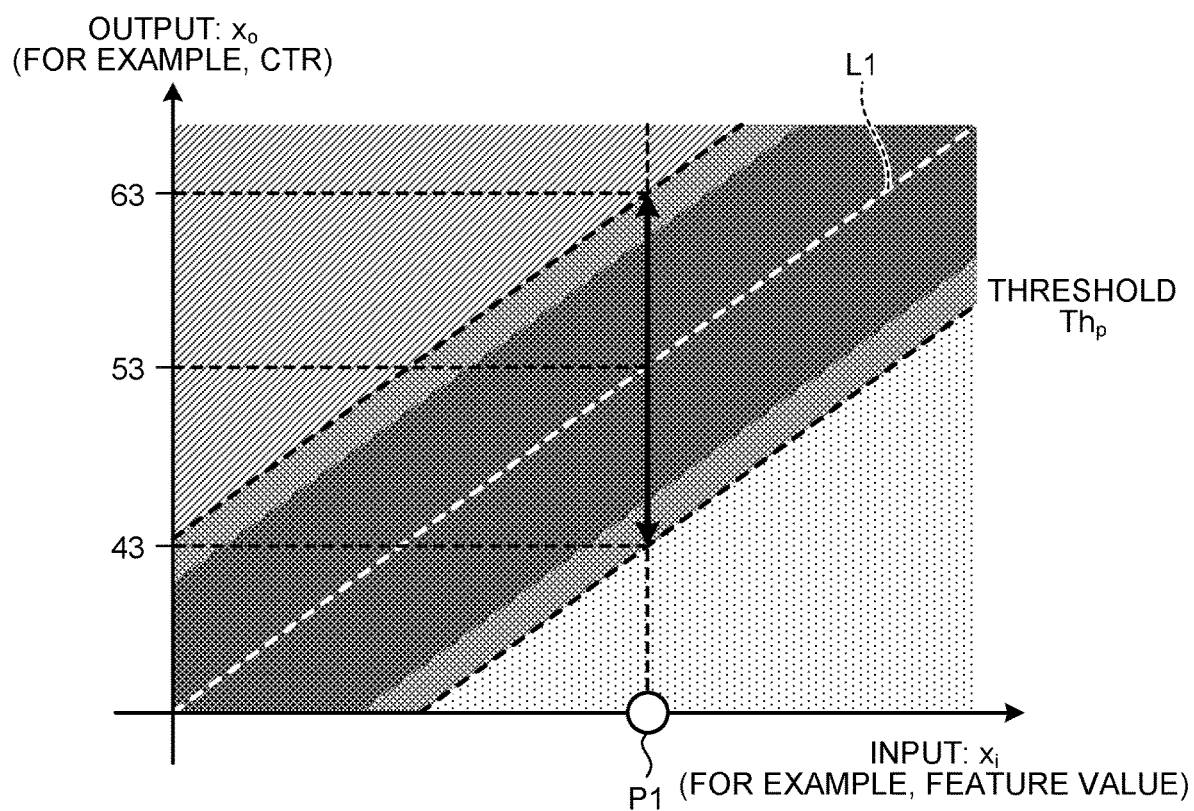
FIG. 10 is diagram for explanation of a range of examination values derived from the conversion function of the first embodiment.

FIG. 10 is a diagram for explanation of a range of random variables derived from a conversion function. FIG. 10 is a diagram schematically illustrating a state of a probability distribution derived from the conversion function. The horizontal axis corresponds to examination values for an examination item $x_i$ to be input and the vertical axis corresponds to examination values for an examination item $x_o$ to be output. FIG. 10 will be described on the assumption that the examination item $x_i$ corresponds to feature values extracted from image information and the examination item $x_o$ is CTR.

For example, in a case where an examination value for the examination item $x_i$ corresponds to a position P1, a possible examination value for the examination item $x_o$ derived from the conversion function is any value in the range of the probability distribution at the position P1. The converting function 254 thus performs processing for narrowing down the examination values for the examination item $x_o$ to one or plural examination values within the range of the probability distribution.

For example, in a case where examination values derived from the conversion function are to be narrowed down to one examination value, the converting function 254 obtains the examination value for the examination item $x_o$ having the highest probability, as a derivation result (conversion result). In the case of FIG. 10, the converting function 254 obtains, as a derivation result, the examination value, "53", for the examination item $x_o$, the examination value corresponding to the position P1 and being on a broken line L1.

Furthermore, for example, in a case where plural examination values derived from the conversion function are to be output, the converting function 254 sets a range (a range indicated by an arrow in FIG. 10) in which the probability is equal to or higher than a threshold $Th_p$, and obtains, as a derivation result, the largest examination value, the smallest examination value, and the examination value having the highest probability, for the examination item $x_o$ in this range. In the case of FIG. 10, the largest examination value for the examination item $x_o$ is "63", the smallest examination value therefor is "43", and the examination value with the highest probability is "53". With respect to this embodiment, description will be made on the assumption that plural examination values are derived from a conversion function.

The converting function 254 then outputs each of the examination values derived for the lacking examination item, to the generating function 255. Specifically, the converting function 254 outputs the examination values derived for the lacking examination item in association with characteristic information indicating characteristics of the examination values in the probability distribution, to the generating function 255. The characteristic information indicates, for example, that the examination values are the above described largest value, smallest value, and examination value with the largest probability.

The converting function 254 may narrow down the conversion functions to be retrieved, according to the number of days corresponding to dates included in the diagnosis and treatment information D1 on the target patient. For example, if the diagnosis and treatment information D1 on the target patient has a single date, the converting function 254 may narrow down the conversion functions to the conversion function calculated by the first calculation method or third calculation method described above. Furthermore, if the diagnosis and treatment information D1 on the target patient has dates for two or more days, the converting function 254 may narrow down the conversion functions to the conversion function calculated by the second calculation method described above.

The generating function 255 in FIG. 3 is an example of a generating unit. The generating function 255 generates, on the basis of an inference obtained by input of an examination value for an examination item included in the diagnosis and treatment information D1 on a target patient into the trained model M1 to be used, support information for supporting diagnosis and treatment of the target patient.

The trained model M1 to be used may be specified via the input interface 21 or communication interface 23, or may be set beforehand. With respect to this embodiment, the trained model M1 to be used is described as the trained model M1 that has been stored in the inference apparatus 30b.

Specifically, the generating function 255 makes a comparison between an examination item included in the diagnosis and treatment information D1 input from the second obtaining function 253, with a requirement (an examination item) for input data to the trained model M1 to be used. In a case where the examination item included in the diagnosis and treatment information D1 on the target patient does not satisfy the requirement for the trained model M1 as a result of the comparison, that is, in a case where there is any lacking examination item in the diagnosis and treatment information D1 on the target patient, the generating function 255 notifies the converting function 254 of the lacking examination item. By using the conversion function described above, the converting function 254 implements derivation of an examination value for the lacking examination item reported by the generating function 255, from an examination value for an existing examination item, and inputs a result of the derivation to the generating function 255.

When the generating function 255 obtains the examination value for the lacking examination item from the converting function 254, the generating function 255 generates a diagnosis and treatment information table having the examination value for the existing examination item included in the diagnosis and treatment information D1 on the target patient, in combination with the examination value for the examination item obtained from the converting function 254, these examination values having been combined together.

FIG. 11 is a diagram illustrating an example of a diagnosis and treatment information table. The diagnosis and treatment information table is a storage unit for storing therein the diagnosis and treatment information D1 on a target patient, for example, the diagnosis and treatment information D1 having been held in the storage 24, for example. FIG. 11 illustrates an example in which the number of target patients is three (patient IDs, "1001", "1002", and "1003"). Furthermore, FIG. 11 illustrates an example of a case where "Blood pressure" and "Image information" are included as existing examination items included in the diagnosis and treatment information D1.

For example, in a case where examination values for the examination items, "Blood pressure" and "CTR", have been prescribed as input data for the trained model M1, "CTR" is the lacking examination item in the diagnosis and treatment information D1 illustrated in FIG. 11. In this case, the generating function 255 notifies the converting function 254 of the lacking examination item, "CTR". Furthermore, in this case, the converting function 254 executes processing for deriving examination values for the lacking examination item, CTR", from the existing image information included in the diagnosis and treatment information D1 by using a conversion function calculated by the third calculation method described above.

When the generating function 255 obtains a result of the derivation of the examination values for the examination item, "CTR", from the converting function 254, the generating function 255 combines the result with the diagnosis and treatment information D1 on the corresponding target patients and stores the combined result and diagnosis and treatment information D1 in the diagnosis and treatment information table, as illustrated in FIG. 11. In FIG. 11, the existing examination items, "Pressure" and "Image information", included in the diagnosis and treatment information D1 and the examination item, "CTR", derived from the converting function 254 are hatched with line styles different from each other. Furthermore, the arrows in FIG. 11 indicate that the examination values for the examination item, "CTR", have been derived from the examination item, "Image information".

If a plural number of examination values are derived by the converting function 254, as illustrated in FIG. 11, each of the examination values are registered in the diagnosis and treatment information table. Specifically, FIG. 11 illustrates the examination values with the largest probability as "Estimate", the smallest examination values in the range of probability equal to and higher than the threshold $Th_p$ as "Smallest", and the largest examination values in the range of probability equal to or higher than the threshold $Th_p$ as "Largest".

When the generating function 255 stores the diagnosis and treatment information D1 on the target patients and results of the derivation by the converting function 254 in the diagnosis and treatment information table, the generating function 255 inputs the examination values for the examination items, "Blood pressure" and "CTR", into the trained model M1 and obtains an inference by the trained model M1. In more detail, for each characteristic of the examination values for the examination item, "CTR", by inputting, together with the examination value for the examination item, "Blood pressure", the examination value with that characteristic, into the trained model M1, the generating function 255 obtains, for that characteristic of the examination values for the examination item, CTR", an inference by the trained model M1.

For example, when examination values for blood pressure and CTR are input to the trained model M1, the trained model M1 outputs, as an inference, the name (disease name) of a disease inferred from the relation between these examination values and a risk value quantitatively indicating the possibility of having that disease or the incidence rate. The generating function 255 then generates support information on the basis of the inference for each characteristic of the examination values inferred by the trained model M1, and registers the support information generated, into a support information table.

FIG. 12 is a diagram illustrating an example of the support information table. The support information table is a storage unit for holding support information stored in the storage 24, for example.

The support information table in FIG. 12 has support information obtained by inputting the examination values for the examination items, "Blood pressure" and "CTR", illustrated in the diagnosis and treatment information table of FIG. 11, into the trained model M1. For example, FIG. 12 illustrates that for the target patient having the patient ID, "1001", the disease name, "Heart failure", has been inferred from the examination values for the examination items, "Blood pressure" and "CTR", for this target patient. Furthermore, the risk values inferred for the examination values for "CTR (Estimate)", "CTR (Smallest)", and "CTR (Largest)" have been registered in association with the disease name.

In FIG. 12, "Risk (Estimate)" means the risk value inferred from the examination value for "CTR (Estimate)". Furthermore, for "Risk (Minimum)" and "CTR when risk is minimum", the smaller one of the risk values inferred for "CTR (Smallest)" and "CTR (Largest)" and the examination value for CTR corresponding to that risk value are registered respectively. In the example of FIG. 12, the risk value is minimum when the examination value for CTR is 45. Furthermore, for "Risk (Maximum)" and "CTR when risk is maximum", the larger one of the risk values inferred for "CTR (Smallest)" and "CTR (Largest)" and the examination value for CTR corresponding to that risk value are registered respectively. In the example of FIG. 12, the risk value is maximum when the examination value for CTR is 63.

In a case where the risk value inferred from the examination value for "CTR (Estimate)" is minimum, the risk value may be registered for the item, "Risk (Minimum)" and the examination value for "CTR (Estimate)" may be registered for the item, "CTR when risk is minimum". Furthermore, similar registration may be performed when the risk value inferred from the examination value for "CTR (Estimate)" is maximum.

On the basis of the diagnosis and treatment information D1 and support information registered in the diagnosis and treatment information table and support information table, the display configuring function 256 generates a display configuration table on which a screen displayed by the displaying function 257 described later is based.

Specifically, on the basis of the registered content in the diagnosis and treatment information table and the registered content in the support information table, the display configuring function 256 generates a display configuration table that has been reconfigured from the registered content in both of these tables.

FIG. 13 is a diagram illustrating an example of a data configuration of the display configuration table. As illustrated in FIG. 13, the display configuration table has the registered content in the diagnosis and treatment information table illustrated in FIG. 11 and the registered content in the support information table illustrated in FIG. 12 in association with each other on the basis of the patient IDs of the target patients and the dates. That is, the display configuration table includes the examination values for the existing examination items, "Blood pressure" and "Image information", obtained for the target patients, the examination values for "CTR" derived by the converting function 254, and inferences made for the target patients from these examination values.

Furthermore, FIG. 13 illustrates an example in which the registered content for the examination item, "CTR", registered in the diagnosis and treatment information table has been reconfigured. Specifically, FIG. 13 illustrates an example in which only the examination values for "CTR (Estimate)" with the highest probability, from the examination item, "CTR", illustrated in FIG. 11, have been registered. In addition, in FIG. 13, the probability of the examination values for "CTR (Estimate)" is registered as "Reliability", in association with the examination values for "CTR (Estimate)".

Furthermore, FIG. 13 illustrates an example in which three disease names, "Heart failure", "Lung cancer", and "Diabetes" inferred for the target patient having the patient ID, "1001", are arranged next to each other. These disease names may be those inferred respectively from trained models M1 of different diagnosis and treatment departments or may be those inferred from a single trained model M1. In either of these cases, if there is a lacking examination item, the diagnosis and treatment support apparatus 20 is able to derive an examination value for the lacking examination item using a conversion function and is thus able to be adapted to various trained models M1 flexibly.

The display configuration table generated by the display configuring function 256 is not limited to the example in FIG. 13. For example, an inference (a disease name) with a risk value equal to or less than a threshold may be excluded from the display configuration information. Furthermore, the examination values for "CTR (Smallest)" and "CTR (Largest)" illustrated in FIG. 11 may be registered in the display configuration table.

The displaying function 257 is an example of an output unit. On the basis of the display configuration table generated by the display configuring function 256, the displaying function 257 displays a screen for supporting the diagnosis and treatment of a target patient, on the display 22.

Figure 14:
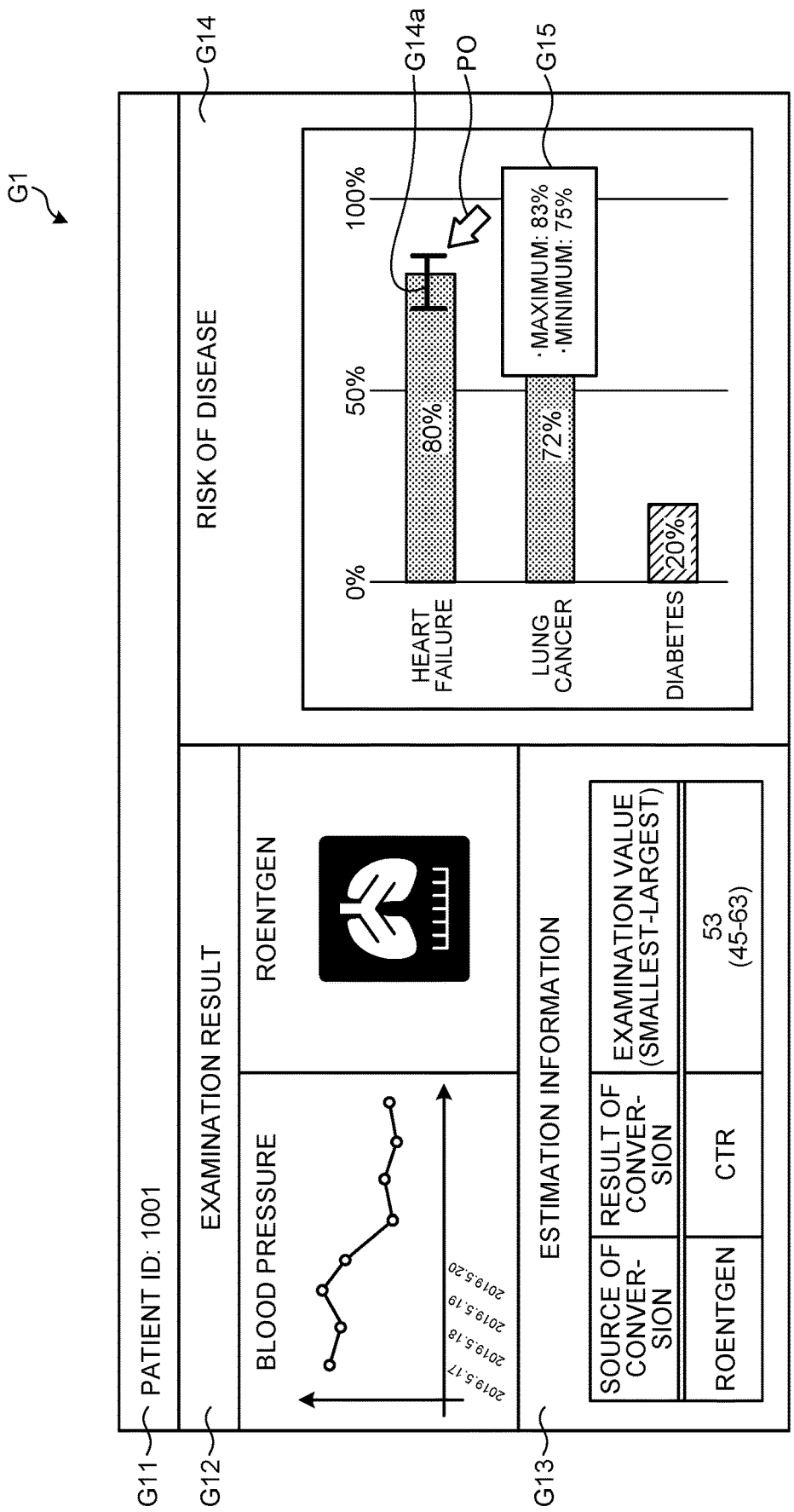
FIG. 14 is a diagram illustrating an example of a screen displayed by a displaying function of the first embodiment.

FIG. 14 is a diagram illustrating an example of a screen displayed by the displaying function 257. FIG. 14 is a screen related to the patient ID, "1001", registered in the display configuration table of FIG. 13.

As illustrated in FIG. 14, a screen G1 has a first area G11 to a fourth area G14. In the first area G11, a patient ID of a target patient registered in the display configuration table is displayed.

In the second area G12, existing diagnosis and treatment information D1 (examination information and image information, for example) registered in the display configuration table is displayed. FIG. 14 illustrates an example in which examination values for blood pressure and a roentgen image that is the image information are displayed. FIG. 14 illustrates the examination values for blood pressure as chronological data, but only an examination value of a particular date may be displayed instead.

In the third area G13, a result of derivation from a conversion function registered in the display configuration table is displayed as estimation information. FIG. 14 illustrates an example in which the estimation information displayed includes "Roentgen" that is the examination item (image information) serving as a source of conversion, "CTR" that is the examination item resulting from the conversion, and the examination values (estimate), (smallest), and (largest) for "CTR".

In the fourth area G14, inferences by the trained model registered in the display configuration table are displayed as risks of diseases. FIG. 14 illustrates an example in which the disease names inferred and the risk values for the disease names are displayed as the risks of diseases by a horizontal bar graph.

The horizontal bar graph is based on risk values for the item, "Risk (Estimate)", and the range of risk values between the "Risk (Minimum)" and "Risk (Maximum)" is represented by a gauge G14a superimposed on the horizontal bar graph. That is, the displaying function 257 displays the plural disease names and risk values inferred by the trained model M1 to be comparable to one another.

Furthermore, the displaying function 257 displays the horizontal bars differently according to the magnitude of the risk values. Specifically, in a case where the risk value is equal to or higher than a threshold (for example, 70%), the displaying function 257 displays the horizontal bar representing that risk value by highlighting the horizontal bar more than any bar graph for a risk value less than the threshold. A user, such as a medical doctor, who sees the screen G1 is thereby able to readily recognize any disease name with a high risk value.

Furthermore, when a mouse pointer PO operated by an operator is moved to the gauge G14a, for example, the displaying function 257 displays the risk values for "Risk (Minimum)" and "Risk (Maximum)" prescribed by this gauge G14a such that these risk values pop up in a window G15.

As described above, the displaying function 257 displays an examination value for an existing examination item included in the diagnosis and treatment information D1 on a target patient and an examination value for an examination item derived by the converting function 254, such that these examination values are able to be distinguished from each other. Furthermore, the displaying function 257 identifiably displays the existing examination item that served as the source of derivation of the examination value for the examination item derived by the converting function 254. In addition, the displaying function 257 comparably displays disease names for a target patient and risk values for the disease names, the disease names and risk values having been inferred by input of an examination value.

The diagnosis and treatment support apparatus 20 is thereby able to let a user, such as a medical doctor, who sees the screen G1 readily know the names of diseases that the target patient possibly has and their risk values, and diagnosis and treatment of the target patient are thus able to be supported efficiently. Furthermore, the diagnosis and treatment support apparatus 20 is able to let the user readily know which examination value for which examination item was lacking for an inference by the trained model M1 that was used. Therefore, on the basis of the screen G1, the user, such as a medical doctor, is able to determine whether to additionally conduct an examination for the lacking examination item according to the disease names and risk values inferred, for example.

A screen displayed by the displaying function 257 is not limited to the screen example illustrated in FIG. 14, and may be displayed in any other display format. For example, the displaying function 257 may display the display configuration table illustrated in FIG. 13 on the display 22. In the case of displaying the display configuration table also, the displaying function 257 preferably displays the disease names by highlighting the disease names according to their risk values, for example. Furthermore, target patients to be displayed may be switched via the input interface 21, for example.

Figure 15:
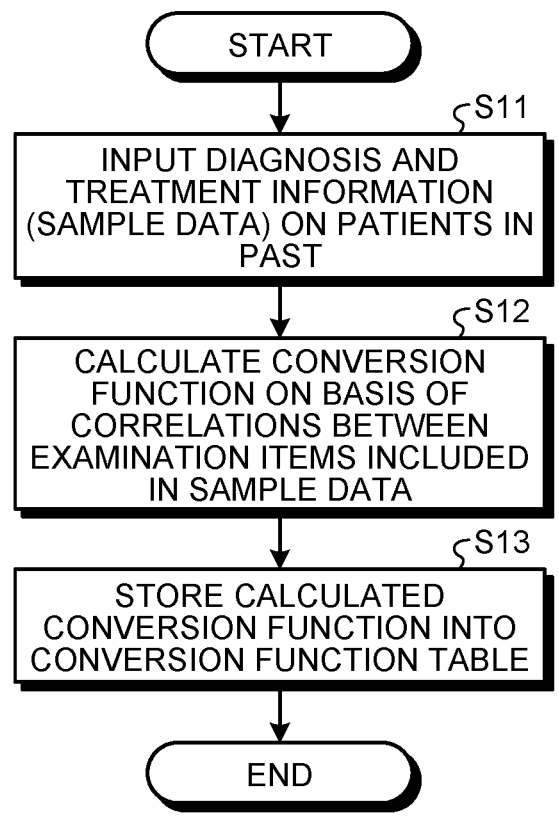
FIG. 15 is a flowchart illustrating an example a conversion function calculating process executed by the diagnosis and treatment support apparatus of the first embodiment.

Operation of the diagnosis and treatment support apparatus 20 will be described below. FIG. 15 is a flowchart illustrating an example of a conversion function calculating process executed by the diagnosis and treatment support apparatus 20.

Firstly, when the first obtaining function 251 obtains sample data that are diagnosis and treatment information D1 on patients in the past stored in a diagnosis and treatment DB 10, the first obtaining function 251 inputs the sample data obtained to the calculating function 252 (Step S11).

The diagnosis and treatment DB 10 serving as a source of obtainment of the sample data is not particularly limited, and for example, may be the diagnosis and treatment DB 10 of a particular diagnosis and treatment department (for example, the first diagnosis and treatment department A) or may be all of diagnosis and treatment DBs 10 respectively provided in different diagnosis and treatment departments.

Furthermore, the sample data obtained by the first obtaining function 251 may be all of the diagnosis and treatment information D1 stored in the diagnosis and treatment DB 10 or only the diagnosis and treatment information D1 corresponding to a condition. The condition for obtaining the sample data may be, for example, a condition related to characteristic information, such as a particular patient (patient ID) or disease name. The condition for obtaining the sample data may be instructed via the input interface 21 or communication interface 23, or may be set beforehand. For example, sample data may be obtained for each disease name.

Furthermore, the timing for the first obtaining function 251 to obtain the sample data is not particularly limited, and the first obtaining function 251 may obtain the sample data at any time. For example, the first obtaining function 251 may start obtaining the sample data when the first obtaining function 251 receives an instruction via the input interface 21. Furthermore, for example, the first obtaining function 251 may obtain the sample data according to a preset schedule. In the latter case, the schedule may set the execution timing to be, for example, once a day or once a week.

Subsequently, on the basis of correlations between examination values for examination items included in the sample data input, the calculating function 252 calculates the conversion function described above for each combination of examination items (Step S12). The calculating function 252 then stores the calculated conversion functions into the conversion function table T1 (Step S13) and ends the process.

Through the conversion function calculating process described above, various conversion functions are stored in the conversion function table T1.

Figure 16:
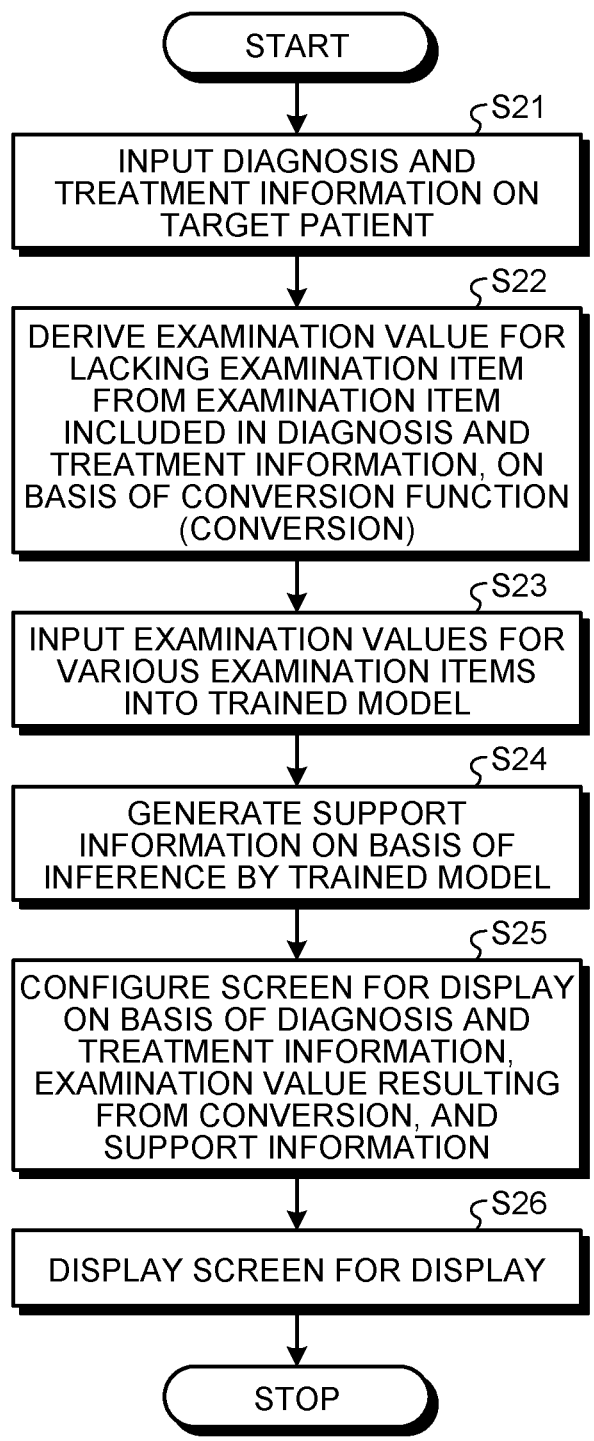
FIG. 16 is a flowchart illustrating an example a diagnosis and treatment support process executed by the diagnosis and treatment support apparatus of the first embodiment.

FIG. 16 is a flowchart illustrating an example of a diagnosis and treatment support process executed by the diagnosis and treatment support apparatus 20. For this process, it is assumed that various conversion functions have been stored in the conversion function table T1.

Firstly, when the second obtaining function 253 obtains the diagnosis and treatment information D1 on a target patient from the diagnosis and treatment DB 10 having the patient ID of the target patient registered therein, the second obtaining function 253 inputs the diagnosis and treatment information D1 obtained, to the converting function 254 and the generating function 255 (Step S21).

The patient ID of the target patient is instructed from an operator, such as a medical doctor, via the input interface 21 or communication interface 23, for example. In a case where the patient ID of the target patient has been registered in plural diagnosis and treatment DBs 10 (for example, the diagnosis and treatment DBs 10a and 10b), the second obtaining function 253 may obtain the diagnosis and treatment information D1 from each of the diagnosis and treatment DBs 10 or may let the operator select the diagnosis and treatment DB 10 (diagnosis and treatment department) from which the diagnosis and treatment information D1 is to be obtained.

When the diagnosis and treatment information D1 is input to the generating function 255, the generating function 255 compares the examination items included in this diagnosis and treatment information D1 with examination items in input data needed for an inference by the inference apparatus 30 (trained model M1), and determines whether or not there is any lacking examination item. If there is any lacking examination item, the generating function 255 notifies the converting function 254 of the lacking examination item.

If there is no lacking examination item, the generating function 255 inputs the examination values for the existing examination items included in the diagnosis and treatment information D1 into the trained model M1 to cause the trained model M1 to infer a disease name, for example. The processing in this case is similar to that by a conventional CDS system or CAD system configuration, and description thereof will thus be omitted.

If there is any lacking examination item, the converting function 254 executes a conversion process for deriving an examination value for the lacking examination item, from the examination values of the existing examination items included in the diagnosis and treatment information D1, on the basis of a conversion function stored in the conversion function table T1 (Step S22).

Subsequently, the generating function 255 inputs the examination values for the existing examination items included in the diagnosis and treatment information D1 and the examination value for the lacking examination item derived at Step S22, into the trained model M1 (Step S23). Subsequently, the generating function 255 generates support information on the basis of an inference output by the trained model M1 (Step S24).

Subsequently, the display configuring function 256 generates a display configuration table for configuring a screen for display, on the basis of the diagnosis and treatment information D1, the examination value resulting from the conversion and derived at Step S22, and the support information generated at Step S24, for example (Step S25). The displaying function 257 then displays the screen for display according to the display configuration table (for example, the screen G1) (Step S26), and ends the process.

As described above, on the basis of correlations between examination values for examination items included in diagnosis and treatment information D1 on plural patients, the diagnosis and treatment support apparatus 20 calculates a conversion function that enables statistical derivation of, from an examination value or values of one or plural examination items, a possible examination value for another examination item. Furthermore, on the basis of an inference obtained by inputting an examination value for an examination item included in diagnosis and treatment information D1 on a target patient into a trained model M1 for inferring information related to a state of the patient from an examination value for an existing examination item, the diagnosis and treatment support apparatus 20 generates support information for supporting diagnosis and treatment of the target patient. In addition, in a case where examination items included in diagnosis and treatment information D1 on a target patient do not satisfy a requirement for a predetermined examination item to be input to a trained model M1, on the basis of a conversion function, the diagnosis and treatment support apparatus 20 derives an examination value for a lacking examination item from examination values for the examination items included in the diagnosis and treatment information D1 on the target patient, and causes the trained model M1 to infer information related to a state of the target patient using the derived examination value for the lacking examination item.

Even if examination items included in diagnosis and treatment information D1 on a target patient do not satisfy a requirement for a trained model M1, for example, the diagnosis and treatment support apparatus 20 is able to obtain an inference by the trained model M1 using an examination value for an examination item derived on the basis of a conversion function. Furthermore, because the conversion function is calculated on the basis of correlations between the examination values for the respective examination items, the diagnosis and treatment support apparatus 20 is able to derive an examination value that is statistically significant.

As described above, the diagnosis and treatment support apparatus 20 is able to automatically supplement examination results with a lacking examination result from diagnosis and treatment information D1 on a target patient according to specifications of a trained model M1 to be used. Therefore, without conducting any additional examination, the diagnosis and treatment support apparatus 20 is able to obtain an inference by the trained model M1 to be used, and is able to flexibly support the diagnosis and treatment of the patient. The diagnosis and treatment support system 1 is thereby able to readily obtain an inference, such as a disease name for a target patient and a risk value therefor using a trained model M1 of a diagnosis and treatment department that is not the diagnosis and treatment department that the target patient has visited, for example, and thus the diagnosis and treatment support system 1 contributes to early detection of diseases, for example.

The embodiment described above may be implemented by modification through change of some of components or functions included in each apparatus, as appropriate. Some modified examples according to the embodiment described above will be described below as other embodiments. Parts different from those of the embodiment described above will mainly be described below and detailed description of parts that are the same as those described already will be omitted. The modified examples described below may be implemented individually or may be implemented in combination, as appropriate.

First Modified Example

In the above described embodiment, the diagnosis and treatment support apparatus 20 executes the process related to calculation of a conversion function and the process related to derivation of an examination value using the conversion function, but these processes may be executed respectively by different apparatuses.

In this case, the apparatus (hereinafter, referred to as the diagnosis and treatment information processing apparatus) that executes the process related to calculation of a conversion function includes a hardware configuration similar to that in FIG. 2 and has the first obtaining function 251 and the calculating function 252 described above. Furthermore, the apparatus (hereinafter, referred to as the diagnosis and treatment support apparatus) that executes the process related to derivation of an examination value using the conversion function includes a hardware configuration similar to that in FIG. 2 and has the above described second obtaining function 253, converting function 254, generating function 255, display configuring function 256, and displaying function 257.

That is, the diagnosis and treatment support apparatus in a diagnosis and treatment support system 1 according to this modified example derives an examination value for a lacking examination item from diagnosis and treatment information D1 on a target patient, by using a conversion function calculated by the diagnosis and treatment information processing apparatus. The diagnosis and treatment support system 1 according to this modified example is thereby able to achieve functions and effects similar to those of the above described embodiment to flexibly support diagnosis and treatment of patients.

Second Modified Example

In the above described embodiment, the diagnosis and treatment support apparatus 20 receives input of specification of a target patient or a trained model M1 via the input interface 21, but without being limited thereto, input of specification of a target patient or a trained model M1 may be received from an external apparatus other than the diagnosis and treatment support apparatus 20. For example, the diagnosis and treatment support apparatus 20 may receive input of specification of a target patient or a trained model M1 from a terminal apparatus provided in a first diagnosis and treatment department A or a second diagnosis and treatment department B and not illustrated in the drawings, via the communication interface 23. Furthermore, for example, the second obtaining function 253 of the diagnosis and treatment support apparatus 20 may obtain diagnosis and treatment information D1 on a target patient transmitted from an external apparatus via the communication interface 23.

In addition, in the above described embodiment, the displaying function 257 outputs the diagnosis and treatment information D1 on a target patient, the derivation result (conversion result) by the converting function 254, and the content of the support information (the support information table) generated by the generating function 255, by displaying them on the display 22, but the method of outputting these pieces of information is not limited to such display.

For example, the displaying function 257 may output (store) a screen based on a display configuration table into the storage 24. Furthermore, the displaying function 257 may output (transmit) a screen based on a display configuration table, to an external apparatus via the communication interface 23.

In addition, data to be output are not limited to a screen based on a display configuration table. For example, a diagnosis and treatment information table or support information table generated by the generating function 255 may be output to the display 22 or an external apparatus. In this case, by cooperating with the displaying function 257, for example, the generating function 255 may function as an example of an output unit.

Third Modified Example

In the above described embodiment, the diagnosis and treatment support apparatus 20 infers information related to a state of a target patient using the diagnosis and treatment DB 10 and inference apparatus 30 that are provided in each of the diagnosis and treatment departments (the first diagnosis and treatment department A and the second diagnosis and treatment department B). However, the configuration of the diagnosis and treatment support system 1 is not limited to this example. For example, the diagnosis and treatment support apparatus 20 may infer information related to a state of a target patient using a diagnosis and treatment DB 10 and an inference apparatus 30 that are provided in each of medical facilities, such as hospitals.

Second Embodiment

In the embodiment described above, the trained model M1 has been trained beforehand, but a training process may be performed in the course of the series of processes executed in a diagnosis and treatment support apparatus 20. This diagnosis and treatment support apparatus 20 according to a second embodiment will be described below. The same reference signs will be assigned to elements that are the same as those of the first embodiment and description thereof will be omitted.

Figure 17:
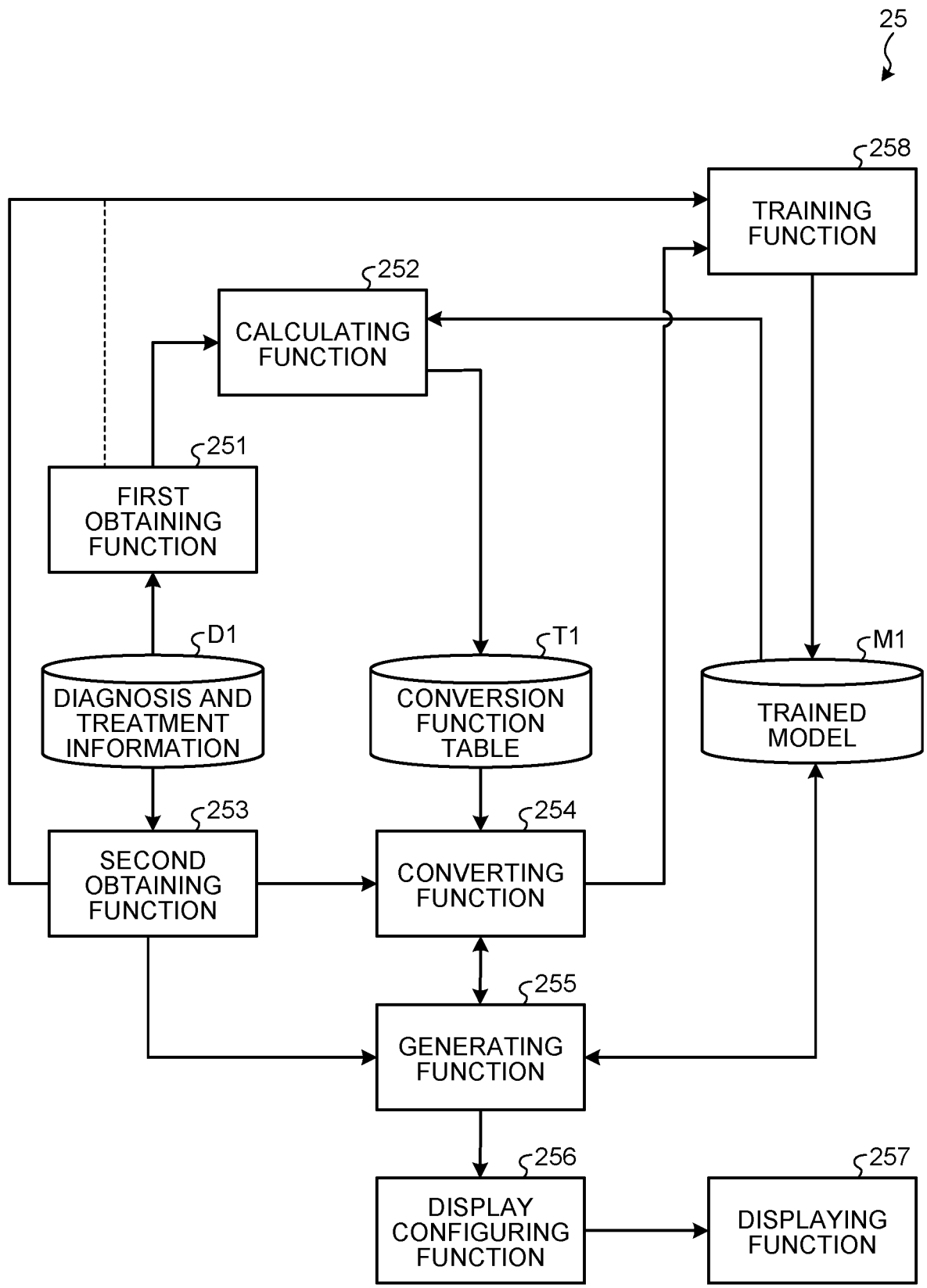
FIG. 17 is a diagram illustrating an example of components included in processing circuitry of a diagnosis and treatment support apparatus according to a second embodiment.

FIG. 17 is a diagram illustrating an example of components included in processing circuitry 25 of the diagnosis and treatment support apparatus 20 according to the second embodiment. The processing circuitry 25 according to this embodiment has, in addition to the functions described by reference to FIG. 3, a training function 258. This training function 258 has been stored in a storage 24 in the form of a program executable by a computer, for example.

The training function 258 is an example of a training unit. The training function 258 executes a training process for a trained model M1. Specifically, the training function 258 executes additional training (such as fine tuning) of the trained model M1 with data for training that are examination values for examination items included in diagnosis and treatment information obtained by the second obtaining function 253 and an examination value for another examination item derived by the converting function 254 from the examination values. In this case, training data (disease names, for example) that may be used are, for example, those input by an operator of the diagnosis and treatment support apparatus 20 or those selected from inferences displayed by the displaying function 257.

Input of diagnosis and treatment information to the training function 258 may be performed by the first obtaining function 251 as indicated by a broken line in FIG. 17. Furthermore, the trained model M1 to be subjected to the additional training is not particularly limited and may be freely set.

Figure 18:
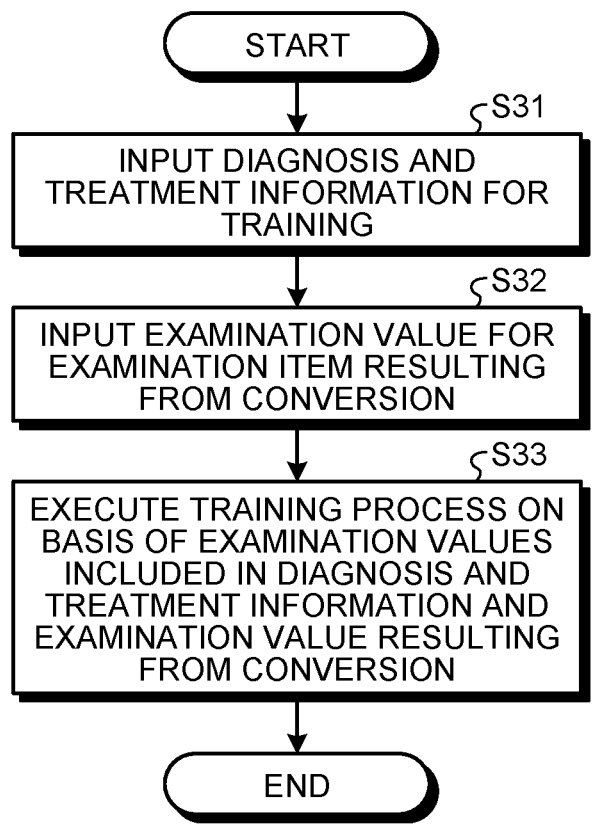
FIG. 18 is a flowchart illustrating an example a training process executed by the diagnosis and treatment support apparatus of the second embodiment.

By reference to FIG. 18, operation of the diagnosis and treatment support apparatus 20 of the second embodiment will be described next. FIG. 18 is a flowchart illustrating an example of a training process executed by the diagnosis and treatment support apparatus 20 of the second embodiment.

Firstly, the second obtaining function 253 obtains diagnosis and treatment information for training, from a diagnosis and treatment DB 10 and input the diagnosis and treatment information to the converting function 254 and training function 258 (Step S31). The diagnosis and treatment information for training is not particularly limited, and may be the above described diagnosis and treatment information on a target patient, for example.

By cooperating with the generating function 255, the converting function 254 derives (by conversion) an examination value for a lacking examination item from the diagnosis and treatment information input at Step S31, the lacking examination item lacking in examination items serving as input parameters for a trained model M1 to be trained. The converting function 254 then inputs the examination value for the examination item resulting from the conversion, to the training function 258 (Step S32).

Subsequently, on the basis of the examination values for the examination items included in the diagnosis and treatment information and the examination value for the examination item resulting from the conversion by the converting function 254, the training function 258 executes a training process for additional training of the trained model M1 (Step S33).

A diagnosis and treatment support system according to the second embodiment is thereby able to use the derivation result by the converting function 254 in the training of the trained model M1. Therefore, the diagnosis and treatment support system 1 according to the second embodiment enables maintenance of the specialty of the trained model M1 specialized for each diagnosis and treatment department and additional learning of trained models using the latest diagnosis and treatment information.

With respect to the above described embodiments, an example of the case where the functional configuration of the diagnosis and treatment support apparatus 20 is implemented by the processing circuitry 25 has been described, but the embodiments are not limited to this example. For example, the functional configurations disclosed in this specification may be implemented by hardware only, or a combination of hardware and software.

In addition, the term, "processor", used in the description above means, for example: a central processing unit (CPU); a graphics processing unit (GPU); or a circuit, such as an application specific integrated circuit (ASIC) or a programmable logic device (for example, a simple programmable logic device (SPLD), a complex programmable logic device (CPLD), or a field programmable gate array (FPGA)). In a case where the processor is a CPU, for example, the processor implements the functions by reading and executing the programs stored in the storage 24. In a case where the processor is, for example, an ASIC, instead of the programs being stored in the storage 24, the functions are directly incorporated, as logic circuits, in the circuit of the processor. Each of the processors according to the embodiments is not necessarily configured as a single circuit, and plural independent circuits may be combined together to be configured as a single processor to implement their functions. Furthermore, plural components in each drawing may also be integrated into a single processor to implement their functions.

The programs executed by the processors are provided by being incorporated in a read only memory (ROM) or a storage, for example, beforehand. These programs may each be provided by being recorded in a computer-readable storage medium, such as a compact disk-ROM (CD-ROM), a flexible disk (FD), a CD-recordable (CD-R), or a digital versatile disc (DVD), in a file having a format installable or executable in these apparatuses. The programs may also be provided or distributed by being stored on a computer connected to a network, such as the Internet, and being downloaded via the network. For example, these programs may be configured as modules including the above described functional units. As to actual hardware, by a CPU reading and executing the programs from a storage medium, such as a ROM, the modules are loaded and generated on a main storage apparatus.

At least one of the embodiments described above enables more flexible support for diagnosis and treatment of patients.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A diagnosis and treatment support system for re-training a previously trained model, comprising:
   a storage apparatus that stores the trained model, which infers information related to a state of a patient from an examination value for a predetermined examination item, wherein the trained model was previously trained using information from patients other than a target patient; and processing circuitry configured to:
  calculate, based on correlations between examination values for plural examination items included in diagnosis and treatment information on plural patients, a conversion function that enables statistical derivation of a value from an examination value or values of one or plural examination items, the value being a possible examination value for another examination item;
  store, in an electronic memory, the conversion function in association with an index value, the index value quantitatively representing a condition as to the examination items used for calculation of the conversion function;
  generate, based on an inference obtained by inputting an examination value for a first examination item included in diagnosis and treatment information on the target patient into the trained model, support information for supporting diagnosis and treatment of the target patient;
  in a case where examination items included in the diagnosis and treatment information on the target patient do not satisfy a requirement for the predetermined examination item,
    derive an examination value for a second examination item not included in the diagnosis and treatment information on the target patient from an examination value for the first examination item included in the diagnosis and treatment information on the target patient, by using one conversion function of stored conversion functions, the one conversion function outputting the derived examination value for the second examination item, and
    select the one conversion function for use based on the associated index value when there are two or more conversion functions allowing derivation of the examination value for the second examination item;
  cause the trained model to infer the information related to a state of the target patient by together inputting the derived examination value for the second examination item and the examination value for the first examination item into the trained model; and
  re-train the previously trained model, based on the derived examination value for the second examination item and the examination value for the first examination item so that the previously trained model is additionally trained using the derived value of the second examination item related to the target patient.

2. The diagnosis and treatment support system according to claim 1, wherein the processing circuitry is further configured to derive, as the examination value for the lacking examination item, a value with a highest probability, from a probability distribution of possible examination values for the lacking examination item, the probability distribution being derived from the conversion function.

3. The diagnosis and treatment support system according to claim 1, wherein the processing circuitry is further configured to derive, as the examination value for the lacking examination item, each of smallest and largest values in a range where a probability is equal to or higher than a threshold in a probability distribution of possible examination values for the lacking examination item, the probability distribution being derived from the conversion function.

4. The diagnosis and treatment support system according to claim 3, wherein the processing circuitry is further configured to cause the trained model to infer information related to a state of the target patient by inputting each of derived examination values for the lacking examination item into the trained model, for each characteristic of the derived examination values.

5. The diagnosis and treatment support system according to claim 1, wherein the processing circuitry is further configured to output the support information generated.

6. The diagnosis and treatment support system according to claim 5, wherein the processing circuitry is further configured to display a screen based on the support information.

7. The diagnosis and treatment support system according to claim 6, wherein the processing circuitry is further configured to display, on a same screen, the examination value for the examination item included in the diagnosis and treatment information on the target patient, the derived examination value for the lacking examination item, and content of the support information.

8. The diagnosis and treatment support system according to claim 1, wherein the processing circuitry is further configured to comprehensively combine examination items included in the diagnosis and treatment information, and calculate the conversion function for each combination of the examination items.

9. The diagnosis and treatment support system according to claim 1, wherein the processing circuitry is further configured to collect, for each of the patients, the diagnosis and treatment information generated on a same day, and calculate the conversion function using the diagnosis and treatment information collected.

10. The diagnosis and treatment support system according to claim 1, wherein the processing circuitry is further configured to collect, for each of the patients, chronologically consecutive pieces of the diagnosis and treatment information, and calculate the conversion function using the collected chronologically consecutive pieces of the diagnosis and treatment information.

11. The diagnosis and treatment support system according to claim 1, wherein the processing circuitry is further configured to calculate, based on a correlation between wording in description information included in the diagnosis and treatment information and examination values for an examination item related to the wording, a particular conversion function that enables derivation of a probability distribution of possible examination values for the examination item from the wording.

* * * * *